(12) United States Patent
Bernhardt et al.

(10) Patent No.: US 10,760,112 B2
(45) Date of Patent: Sep. 1, 2020

(54) ENZYMATIC ACTIVITY ASSAYS FOR GLUCOCEREBROSIDASE

(71) Applicant: Shire Human Genetic Therapies, Inc., Lexington, MA (US)

(72) Inventors: Peter Bernhardt, Lexington, MA (US); Chen-Chung Willy Yen, Lexington, MA (US); Vijay Chhajlani, Arlington, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 636 days.

(21) Appl. No.: 15/537,296

(22) PCT Filed: Dec. 16, 2015

(86) PCT No.: PCT/US2015/066168
§ 371 (c)(1),
(2) Date: Jun. 16, 2017

(87) PCT Pub. No.: WO2016/100556
PCT Pub. Date: Jun. 23, 2016

(65) Prior Publication Data
US 2018/0051315 A1 Feb. 22, 2018

Related U.S. Application Data

(60) Provisional application No. 62/093,818, filed on Dec. 18, 2014.

(51) Int. Cl.
*C12Q 1/40* (2006.01)
*C12Q 1/34* (2006.01)

(52) U.S. Cl.
CPC .......... *C12Q 1/40* (2013.01); *C12Q 1/34* (2013.01); *C12Y 302/01045* (2013.01); *G01N 2333/924* (2013.01); *G01N 2500/20* (2013.01)

(58) Field of Classification Search
CPC ..................................................... C12Q 1/40
USPC ........................................................ 702/19
See application file for complete search history.

(56) References Cited

U.S. PATENT DOCUMENTS

2014/0274798 A1  9/2014  Cherkassky et al.

OTHER PUBLICATIONS

Brumshtein, B. et al., Characterization of gene-activated human acid-beta-glucosidase: crystal structure, glycan composition, and internalization into macrophages, Glycobiology, 20(1): 24-32 (2010).
Calias, P. et al., CNS Penetration of Intrathecal-Lumbar Idursulfase in the Monkey, Dog and Mouse: Implications for Neurological Outcomes of Lysosomal Storage Disorder, PLoS One, 7(1): e30341 1-13 (2012).
Dinur, T. et al., Synthesis of fluorescent derivative of glucosyl ceramide for the sensitive determination of glucocerebrosidase activity, Analytical Biochemistry, 136(1): 223-234 (1984).
Hayashi, Y. et al., A sensitive and reproducible fluorescent-based HPLC assay to measure the activity of acid as well as neutral beta-glucocerebrosidases, Analytical Biochemistry, 383(1): 122-129 (2008).
International Search Report for PCT/US2015/066168, 6 pages (dated Apr. 19, 2016).
Osiecki-Newman, K. et al., Humanacid beta-glucosidase: use of inhibitors, alternative substrated and amphiphiles to investigate the properties of the normal and Gaucher disease active sites, Biochimica et Biophysica Acta, 915: 87-100 (1987).
Voznyi, Y.V. et al., A fluorimetric enzyme assay for the diagnosis of MPS II (Hunter disease), J. Inherit. Metab. Dis., 24: 675-680 (2001).
Written Opinion for PCT/US2015/066168, 6 pages (dated Apr. 19, 2016).
Zimran, A., Velaglucerase alfa: A new option for Gaucher disease treatment, Drugs of Today, 47(7): 515 (2011).

*Primary Examiner* — Jerry Lin
(74) *Attorney, Agent, or Firm* — Charles E. Lyon; David E. Shore; Choate, Hall & Stewart LLP

(57) ABSTRACT

The present invention provides, among other things, methods and compositions for determining enzyme kinetic parameters (e.g., Vmax, Km, and specific activity, etc.) indicative of clinically relevant properties of glucocerebrosidase using a physiologically relevant substrate, in particular, a substrate that is representative of substrates that typically accumulate in patients suffering from Gaucher disease such as glucosylceramide. Thus, the present invention is particularly useful to measure a kinetic parameter relating to the activity of glucocerebrosidase in a drug substance, drug product, and stability sample for enzyme replacement therapy.

28 Claims, 7 Drawing Sheets

Specification includes a Sequence Listing.

ENZYMATIC ACTIVITY ASSAYS FOR GLUCOCEREBROSIDASE

CROSS-REFERENCE TO RELATED APPLICATIONS

This application is a National Stage Application based on International Application No. PCT/US2015/066168, filed Dec. 16, 2015, which claims the benefit of U.S. Provisional Application No. 62/093,818, filed Dec. 18, 2014, the contents of each of which is hereby incorporated by reference in its entirety.

BACKGROUND

Glucocerebrosidase enzyme is typically capable of breaking down glucosylceramide into the products glucose and ceramide. Deficiency of glucocerebrosidase, e.g., due to mutation of GBA, can result in clinical phenotypes. Specifically, deficiency of glucocerebrosidase can lead to the progressive accumulation of glucosylceramide within macrophages, predominantly in spleen, liver, and bone marrow, potentially leading to hepatosplenomegaly, anemia, thrombocytopenia, and skeletal involvement.

Gaucher disease is a condition associated with the absence or dysfunction of glucocerebrosidase. The incidence of Gaucher disease is about 1 in 20,000 live births. The most common symptoms of Gaucher disease are enlargement of the liver and spleen, anemia, nose bleeds, reduced platelets (resulting in easy bruising and long clotting times), bone pain ("bone crises"), bone deterioration, bone infarctions often leading to damage to the shoulder or hip joints, and a generalized demineralization of the bones (osteoporosis). The weakening of the bones can then lead to spontaneous fractures. The course of the disease is quite variable: while some affected individuals display no outward symptoms, Gaucher disease can result in severe disability and death in others.

Over 350 mutations of GBA have been detected in patients with Gaucher disease. Missense mutations are the most common type of mutation. Mutations can disrupt trafficking, stability, processing, a variety of other parameters, or a combination thereof. GBA mutations can be classified as mild, severe, or lethal, on the basis of biochemical and physiological outcomes. The estimated prevalence rate of Gaucher disease is 1 in 50,000 to 1 in 100,000 in the general population, and 1 in 855 in the Ashkenazi Jewish population. In individuals of Ashkenazi Jewish descent, the carrier frequency has been estimated to be as high as approximately 1 in 15.

An important treatment for Gaucher disease is enzyme replacement therapy. For example, velaglucerase alfa (trade name VPRIV™), manufactured by Shire plc, is a recombinant form of glucocerebrosidase approved by FDA as a long-term enzyme replacement therapy for those suffering of Gaucher disease.

SUMMARY

The present invention provides, among other things, improved methods for assessing potency of glucocerebrosidase to facilitate enzyme replacement therapy. In particular, the present invention provides enzyme activity assays for velaglucerase alfa and other recombinant forms of glucocerebrosidase using a physiologically relevant substrate, i.e., a substrate that is representative of one or more physiological substrates that accumulate in patients suffering from Gaucher disease. Thus, the present invention permits clinically relevant assessment of recombinant glucocerebrosidase for enzyme replacement therapy.

At least one aspect of the present invention includes a method of determining potency of glucocerebrosidase, including the steps of contacting a sample including a glucocerebrosidase with a substrate containing a glucosylceramide moiety under conditions that permit the glucocerebrosidase to catalyze hydrolysis of the substrate to release glucose and analyzing glucose released to determine one or more kinetic parameters of the glucocerebrosidase, such that the one or more kinetic parameters can be indicative of the potency of the glucocerebrosidase. In some instances, the glucocerebrosidase is a recombinant glucocerebrosidase. In some instances, the recombinant glucocerebrosidase is velaglucerase alfa. In various embodiments, the substrate is defined by a structure of formula I:

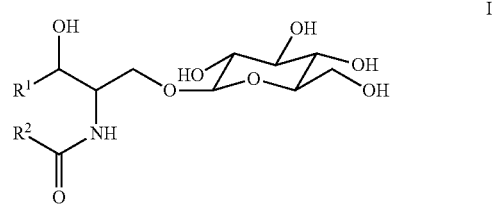

where $R^1$ is a $C_{4-30}$ straight or branched, saturated or unsaturated, hydrocarbon chain optionally substituted with a detectable moiety or one or more hydroxyl groups; and $R^2$ is a $C_{4-30}$ straight or branched, saturated or unsaturated, hydrocarbon chain optionally substituted with a detectable moiety or one or more hydroxyl groups. In various embodiments, the substrate is defined by a structure of formula II:

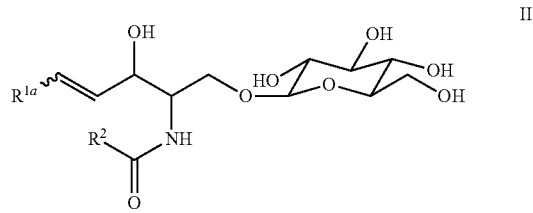

where ⁓ refers to either cis or trans double bond stereochemistry, or a mixture thereof; and $R^{1a}$ is a $C_{2-28}$ straight or branched, saturated or unsaturated, hydrocarbon chain optionally substituted with a detectable moiety or one or more hydroxyl groups; and $R^2$ is a $C_{4-30}$ straight or branched, saturated or unsaturated, hydrocarbon chain optionally substituted with a detectable moiety or one or more hydroxyl groups. In various embodiments, the substrate is defined by a structure of formula II-a:

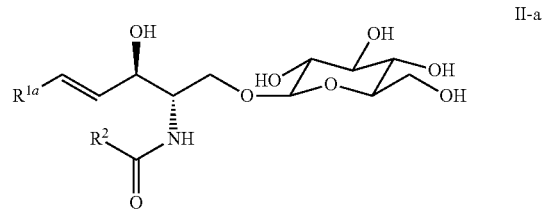

where $R^{1a}$ is a $C_{2-28}$ straight or branched, saturated or unsaturated, hydrocarbon chain optionally substituted with a detectable moiety or one or more hydroxyl groups; and $R^2$ is a $C_{4-30}$ straight or branched, saturated or unsaturated, hydrocarbon chain optionally substituted with a detectable moiety or one or more hydroxyl groups.

In any above embodiments including a detectable moiety, the detectable moiety can be a fluorescent label, for example, a fluorescent label that is or includes NBD-X. In particular examples, the substrate is:

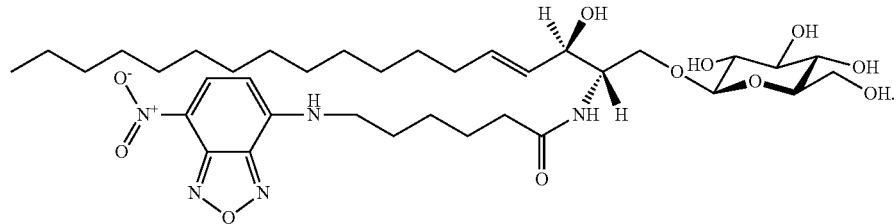

In various embodiments of the present invention, the substrate is defined by a structure of:

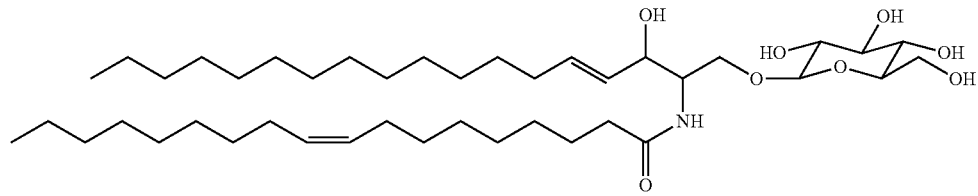 [SMILES: CCCCCCCC/C=C\CCCCCCCC(=O)NC(COC1OC(CO)C(O)C(O)C1O)C(O)/C=C/CCCCCCCCCCCCC]

In various embodiments, the substrate is defined by a structure of:

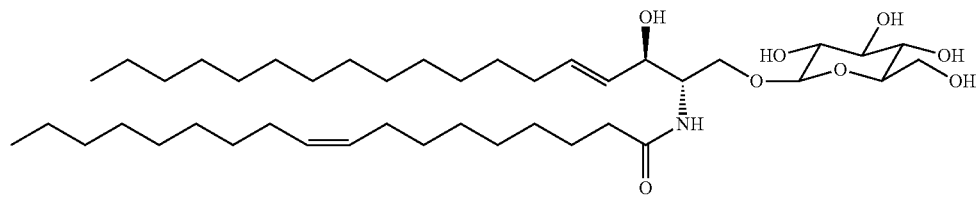 [SMILES: CCCCCCCC/C=C\CCCCCCCC(=O)N[C@@H](COC1OC(CO)C(O)C(O)C1O)[C@H](O)/C=C/CCCCCCCCCCCCC]

In particular embodiments, the substrate is C18:1 β-D-Glucosylceramide.

In various embodiments of the present invention, the step of analyzing the glucose released includes performing chromatography. For example, the chromatography can include high-performance liquid chromatography (HPLC) or ultra performance liquid chromatography (UPLC). In particular embodiments, the chromatography includes anion exchange chromatography. In some embodiments, the step of analyzing the glucose released includes performing high-performance anion exchange chromatography coupled to pulsed amperometric detection (HPAEC-PAD). In various embodiments, the detectable moiety is detectable via chemiluminescence, fluorescence, or ultraviolet/visible absorbance spectroscopy.

In any of the above embodiments, the step of analyzing the glucose released can include determining the amount of glucose as compared to a control such as a pre-determined amount of glucose or by comparison to a standard curve.

In any of the above embodiments, the step of analyzing glucose released can include determining the rate of glucose formation.

In any of the above embodiments, the one or more kinetic parameters can be determined by fitting data obtained from analyzing the product formation to the Michaelis-Menten model or other kinetic model suitable to determine kinetic parameters. For example, the one or more kinetic parameters can be selected from the group consisting of $V_{max}$, $k_{cat}$, $K_m$, specific activity and combination thereof.

In any of the above embodiments, the substrate can be sonicated prior to the contacting. For instance, the substrate can be sonicated for about 1 to 10 minutes.

In any of the above embodiments, the sample can be a drug substance, a drug product, or a stability sample of drug substance and drug product.

In any of the above embodiments, the conditions that permit the glucocerebrosidase to catalyze the substrate to release glucose can include incubation at about 37° C. for about 20 minutes.

In any of the above embodiments, the conditions that permit the glucocerebrosidase to catalyze hydrolysis of the substrate to release glucose can include taurocholic acid and/or oleic acid. In particular embodiments, the taurocholic acid is included, e.g., at a concentration of about 0.5 to 100 mM, e.g., at a concentration of about 2 to 10 mM, e.g., at a concentration of 2 to 7 mM. In various embodiments, the oleic acid is included. For example, the oleic acid can be included at a concentration of about 0.001% to 5% v/v, e.g., at a concentration of about 0.1% to 0.5% v/v, e.g., at a concentration of about 0.1% to 0.3% v/v.

In any of the above embodiments, the method can further include a step of inactivation of the glucocerebrosidase.

In any of the above embodiments, the method can include a step of removing lipids from an enzyme sample prior to analyzing the glucose released. For example, the step of removing lipids can include in-line desalting.

DEFINITIONS

In order for the present invention to be more readily understood, certain terms are first defined below. Additional definitions for the following terms and other terms are set forth throughout the specification.

Batch: As used herein, the term "batch" refers to a completed manufacturing run, in which a product, finished good or component is produced. In some embodiments, a batch comprises multiple "lots". As used herein, the term "lot" refers to a part or fraction of the total completed product produced during the manufacture of a commercial batch. In some embodiments, a batch consists of a single lot. In some embodiments, a batch consists of a plurality of lots. In some embodiments, a batch is partitioned into individual lots based on sample size, FDA requirements and/or shipping conditions. In some embodiments, a batch is partitioned into lots based on specific factions produced during manufacture of the batch.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. Biological activity can also be determined by in vitro assays (for example, in vitro enzymatic assays). In particular embodiments, where a protein or polypeptide is biologically active, a portion of that protein or polypeptide that shares at least one biological activity of the protein or polypeptide is typically referred to as a "biologically active" portion. In some embodiments, a protein is produced and/or purified from a cell culture system, which displays biologically activity when administered to a subject.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control. In some embodiments, the control may be a "reference control", which is a sample used for comparison with a test sample, to look for differences or for the purposes of characterization.

Concentration: As used herein, the term "concentration" refers to a measure indicative of amount of substance in a volume. Typically, concentration is measured by a numerical value with physical units of mass*volume$^{-1}$, such as molar and millimolar.

Enzyme: As used herein, the term "enzyme" refers to any protein capable of producing changes in a biological substance by catalytic action.

Enzyme activity: As used herein, the term "enzyme activity", "enzymatic activity" or grammatical equivalent, refers to the general catalytic properties of an enzyme.

Enzyme assays: As used herein, the term "enzyme assays", "enzymatic assays", "enzymatic activity assays", or grammatical equivalent, refers to procedures for measuring the amounts or activities of enzyme in a sample.

Enzyme reaction: As used herein, the term "enzyme reaction" refers to a chemical process in which an enzyme catalyzes conversion of one or more molecules into different molecules. Molecules at the beginning of the process, are called substrates. Molecules at the end of the process are called products.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodstream. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Kinetic model: As used herein, the term "kinetic model" refers to any quantitative description of enzyme reaction rate. Typically, a kinetic model constitutes an equation to fit kinetic experimental data and/or derive a set of parameters that define an enzymatic reaction. For example, a Michaelis-Menten kinetic model is a common model of a single-substrate reaction. A kinetic model may require, benefit from, or optionally include, in various instances, particular assumptions or requisites for application. Such assumptions or requisites are known in the art with respect to particular kinetic models, e.g., the Michaelis-Menten model.

Kinetic parameter: As used herein, the term "kinetic parameter" means any measure relating to the activity of an enzyme in a particular enzymatic reaction with a particular substrate. As used herein, kinetic parameters include any parameters indicative of reaction rate (e.g., $V_{max}$ and $K_m$, etc.) and specific activity. Under the Michaelis-Menten model, the substrate concentration (denoted as [S]) must be greater than the enzyme concentration (denoted as [E]), and initial rates must be determined for each [S]. $V_{max}$ represents the maximum rate achieved by the system, at maximum (saturating) substrate concentrations. Typically, enzyme-catalyzed reactions are saturable. Their rate of catalysis does not always show a linear response to increasing substrate. If the initial rate of the reaction is measured over a range of substrate concentrations (denoted as [S]), the reaction rate (v) generally increases as [S] increases. However, as [S] gets higher, the enzyme becomes saturated with substrate and the rate reaches $V_{max}$, the enzyme's maximum rate. $K_m$, also known as the Michaelis constant, is the substrate concentration at which the reaction rate is half of $V_{max}$. The parameter $k_{cat}$ is equal to $V_{max}/[E]$.

Specific activity is typically defined as the amount of substrate the enzyme converts (reactions catalyzed), per mg protein in the enzyme preparation, per unit of time. Specific activity can be used as to calculate or estimate activity recovery following purification.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Various other sequence alignment programs are available and can be used to determine sequence identity such as, for example, Clustal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Potency: As used herein, the term "potency" refers to the specific ability or capacity of a product, as indicated by appropriate tests (e.g., an enzymatic kinetic assay described herein), to effect a desired therapeutic result. In some instances, potency is quantitatively indicated by appropriate tests (e.g., an enzymatic kinetic assay described herein). In some instance, potency is qualitatively indicated by appropriate tests (e.g., an enzymatic kinetic assay described herein). For instance, the potency of a product may be indicated by various kinetic parameters including, without limitation, $V_{max}$, $K_m$, $k_{cat}$, specific activity, or any combination thereof, measured by an enzymatic assay described herein. Thus, in some embodiments, an enzymatic kinetic assay described herein may be used as potency test.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Sample: As used herein, the term "sample" means a small part of something intended to show the quality, nature or quantity of the whole thing. The term sample encompasses any sample obtained from any source. For example, a sample containing an enzyme of interest may be obtained from an enzyme production system, enzyme purification process, formulated drug substance, or a biological source.

Standard Curve: As used herein, the term "standard curve" refers to a type of graph used as a quantitative research tool. Typically, multiple samples with known properties are measured and graphed, which then allows the same properties to be determined for unknown samples by interpolation on the graph. The samples with known properties are the standards, and the graph is the standard curve.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. In some embodiments, the phrase "substantially pure" of "substantially purified", refers to a protein (native or recombinant) which is substantially free of contaminating endogenous materials, such as, e.g., other proteins, lipids, carbohydrates, nucleic acids and other biological materials with which it is naturally associated. For example, a substantially pure molecule can be at least about 60%, by dry weight, preferably about 70%, 80%, 90%, 95% or 99% of the molecule of interest.

DETAILED DESCRIPTION

Figure 1:
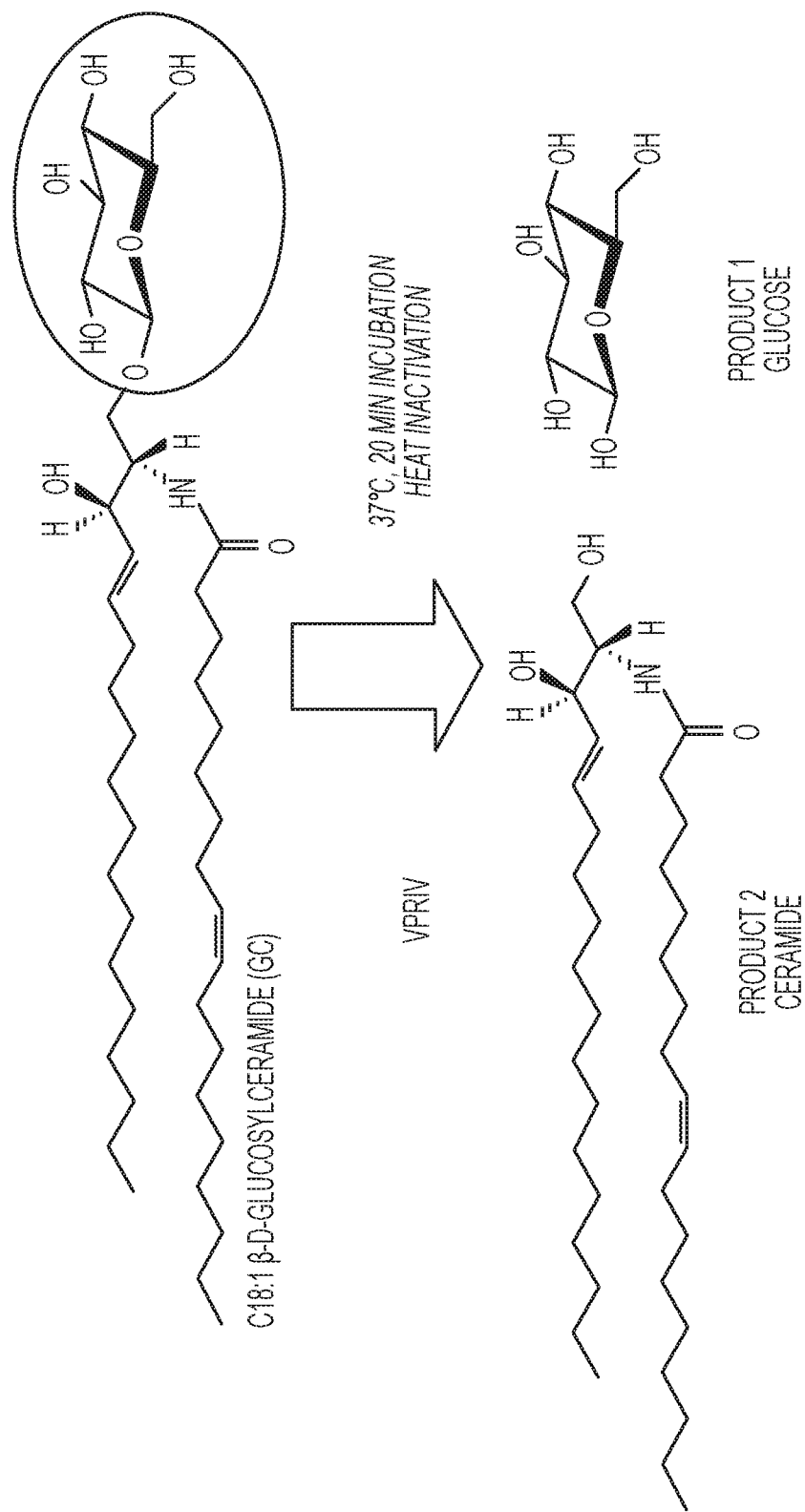
FIG. 1 is an exemplary schematic showing the cleavage of the substrate C18:1 β-D-Glucosylceramide by velaglucerase alfa, resulting in two products: glucose (product 1) and ceramide (product 2).

The present invention provides, among other things, methods and compositions for determining enzyme kinetic parameters (e.g., Vmax, Km, and specific activity, etc.) indicative of clinically relevant properties of glucocerebrosidase using a physiologically relevant substrate, in particular, a substrate that interacts with glucocerebrosidase in a manner representative of one or more substrates that typically accumulate in patients suffering from Gaucher disease. For example, glucocerebrosidase enzyme catalyzes the hydrolysis of glucosylceramide to glucose and ceramide via cleavage of the glucosidic linkage of glucosylceramide.

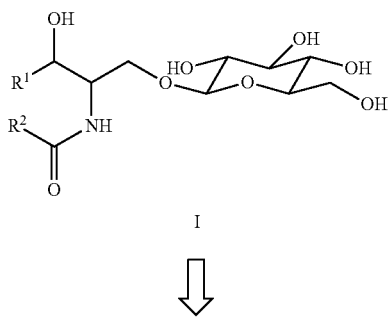

I

⇓

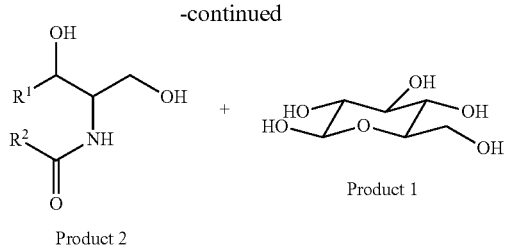

Product 2

Product 1 wherein $R^1$ and $R^2$ are as defined and described herein.

One example of such a physiologically relevant substrate that may be used in the present invention is C18:1 glucosylceramide. Some assays of the present invention may include the use of high performance anion exchange chromatography coupled to pulsed amperometric detection (HPAEC-PAD) to detect one or more reaction products and determine kinetic parameters relating to glucocerebrosidase enzyme.

The present invention is particularly useful to measure the enzyme kinetic parameters of glucocerebrosidase in a drug substance, drug product, or stability sample for enzyme replacement therapy.

Various aspects of the invention are described in detail in the following sections. The use of sections is not meant to limit the invention. Each section can apply to any aspect of the invention. In this application, the use of "or" means "and/or" unless stated otherwise.

Glucocerebrosidase

The present invention may be applied to any glucocerebrosidase, including any recombinant or naturally-occurring glucocerebrosidase. Glucocerebrosidase enzyme can also be referred to as acid β-glucosidase, β-glucosidase, glucosidase, glucosidase β acid, GBA, D-glucosyl-N-acylsphingosine glucohydrolase, glucosylceramidase, or GCase. Glucosylceramide can also be referred to as glucocerebroside. Glucocerebrosidase enzyme can be encoded by the gene GBA. For instance, in humans, GBA-1 is thought to ubiquitously express a glucocerebrosidase enzyme that typically is initially synthesized as a 519 amino acid protein having four co-translationally acquired N-linked glycans. It is thought that, following translation, a 23 amino acid signal peptide is removed from the protein. Glucocerebrosidase enzyme can also include additional posttranslational modifications.

As used herein, the terms "glucocerebrosidase enzyme," "glucocerebrosidase protein," and grammatical equivalents, are used interchangeably. A single sample of glucocerebrosidase enzyme may include multiple forms of the enzyme. The present invention is applicable to naturally-occurring glucocerebrosidase enzymes (e.g., wild-type or mutant forms) or glucocerebrosidase proteins produced through in vivo or in vitro gene or protein recombination, engineering, synthesis, combinations thereof, or other techniques of molecular biology.

In some embodiments, the present invention is applicable to recombinant glucocerebrosidase including, but not limited to the recombinant enzymes known as velaglucerase alfa, alglucerase, imiglucerase, taliglucerase, and ceridase. Velaglucerase alfa is an enzyme indicated for long-term enzyme replacement therapy for pediatric and adult patients with Gaucher disease Type 1. Velaglucerase alfa may also be known as VPRIV®. The sequences of velaglucerase alfa can be:

```
                                                (SEQ ID NO: 1)
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQC

LGFTPEHQRDFIARDLGPTLANSTHEINVRLLMLDDQRLLLPHWAKVVLT

DPEAAKYVHGIAVHWYLDFLAPAKATLGETHRLFPNTMLFASEACVGS

KFWEQSVRLGSWDRGMQYSHSIITNLLYHVVGWTDWNLALNPEGGPN

WVRNFVDS
```

In other instances, a glucocerebrosidase enzyme has the following sequence:

```
                                                (SEQ ID NO: 2)
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHEINVRLLMLDDQRLLLPHWAKVVLTDP

EAAKYVHGIAVHWYLDFLAPAKATLGETHRLFPNTMLFASEACVGSKFWE

QSVRLGSWDRGMQYSHSIITNLLYHVVGWTDWNLALNPEGGPNWVRNFV

DSPIIVDITKDTFYKQPMFYHLGHFSKFIPEGSQRVGLVASQKNDLDAVA

LMHPDGSAVVVVLNRSSKDVPLTIKDPAVGFLETISPGYSIHTYLWRRQ
```

Imiglucerase is recombinant, infusible enzyme that is produced in Chinese hamster ovary cells and differs from the archetypal wild-type human enzyme sequence by a single amino-acid substitution at position 495. Imiglucerase can have the following sequence:

```
                                                (SEQ ID NO: 3)
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKIKIPLIHRALQLAQRPVSLLASPWTSPTWLKTNGAVNGKGSLKGQ

PGDIYHQTWARYFVKFLDAYAEKKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPAKATLGETHRLFPNTMLFASEACVGSKFWEQ

SVRLGSWDRGMQYSHSIITNLLYHVVGWTDWNLALNPEGGPNWVRNFV

DSPIIVDITKDTFYKQPMFYHLGHFSKFIPEGSQRVGLVASQKNDLDAVA

LMHPDGSAVVVVLNRSSKDVPLTIKDPAVGFLETISPGYSIHTYLWRRQ
```

Taliglucerase alfa is a novel plant cell-derived recombinant human glucocerebrosidase enzyme. Taliglucerase alfa is a 506 amino acid enzyme, of which 497 amino acids encode for human glucocerebrosidase. This sequence differs from the archetypal wild-type human glucocerebrosidase enzyme sequence by the addition of amino acids at the N-terminus and C-terminus of the protein. For instance, taliglucerase alfa may differ from human glucocerebrosidase by two amino acids at the N terminus and up to 7 amino acids at the C terminus.

The present invention includes any glucocerebrosidase enzymes provided herein, within the definition of glucocerebrosidase enzyme provided herein, or that may be derived from natural or laboratory-induced mutation of a naturally-occurring glucocerebrosidase or other glucocerebrosidase enzyme.

In some embodiments, a glucocerebrosidase enzyme suitable for the present invention is any protein or a portion of a protein (e.g., comprising at least 30, 35, 40, 45, 50, 60, 70, 80, 90, 100, 200, 300, 400, 450, 500, 525, 550, or more, or all amino acids) having at least 70% homology or identity (e.g., 70, 71, 72, 73, 74, 75, 80, 85, 90, 95, or 100% homology or identity) to a naturally-occurring or recombinant glucocerebrosidase enzyme, including, but not limited to, those recombinant glucocerebrosidase proteins described herein such as velaglucerase alfa, alglucerase, imiglucerase, taliglucerase, and ceridase. In some embodiments, a glucocerebrosidase enzyme suitable for the present invention is any protein or a portion of a protein (e.g., comprising at least 30, 35, 40, 45, 50, 60, 70, 80, 90, 100, 200, 300, 400, 450, 500, 525, 550, or more, or all amino acids) having at least 70% homology or identity (e.g., 70, 71, 72, 73, 74, 75, 80, 85, 90, 95, or 100% homology or identity) to SEQ ID NO:1, SEQ ID NO:2, or SEQ ID NO:3.

Enzyme Samples

Samples of glucocerebrosidase enzyme may be derived from a variety of sources. Samples of glucocerebrosidase enzyme can include, without limitation, drug substance, drug product, samples derived from cell lines, cell lines, stored samples, or in-process samples. A suitable sample for the present invention may contain glucocerebrosidase in any form (e.g., isolated or not, purified or unpurified). In particular embodiments, a suitable sample for the present invention is a sample containing a purified glucocerebrosidase for enzyme replacement therapy, also referred to as replacement glucocerebrosidase enzyme. Such a sample may be a drug substance, drug product, or a stability sample. Purified replacement glucocerebrosidase may be recombinant, synthetic, gene-activated or natural enzyme.

In some embodiments, a suitable sample for the present invention contains recombinant glucocerebrosidase. As used herein, the term recombinant glucocerebrosidase refers to any glucocerebrosidase produced using a recombinant technology. Suitable expression systems for recombinant technology include, for example, egg, baculovirus, plant, yeast, or mammalian cells. In some embodiments, a recombinant glucocerebrosidase is produced by cells engineered to express glucocerebrosidase. Typically, cells encoding a glucocerebrosidase enzyme may be cultured under standard cell culture conditions such that glucocerebrosidase enzyme is produced by the cells.

In some embodiments, glucocerebrosidase enzymes are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59,1977); human fibrosarcoma cell line (e.g., HT1080); baby hamster kidney cells (BHK21, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383: 44-68, 1982); MRC 5 cells; FS4 cells; and a human hepatoma line (Hep G2).

In some embodiments, recombinant glucocerebrosidase enzymes produced from human cells (e.g., HT1080) are purified. In some embodiments, recombinant glucocerebrosidase enzymes produced from CHO cells are purified.

Typically, cells that are engineered to express recombinant glucocerebrosidase may comprise a transgene that encodes a glucocerebrosidase protein described herein. It should be appreciated that the nucleic acids encoding glucocerebrosidase may contain regulatory sequences, gene control sequences, promoters, non-coding sequences and/or other appropriate sequences for expressing the glucocerebrosidase. Typically, the coding region is operably linked with one or more of these nucleic acid components. A glucocerebrosidase sample may be purified according to any of a variety of methods known in the art.

In some instances, a sample is taken from an organism and contains a naturally-occurring glucocerebrosidase. Such a sample may be derived, for example, from a tissue sample (e.g., a tissue biopsy, e.g. an organ biopsy), from drawn blood, from bodily fluids, from cells, or by other means known in the art. A glucocerebrosidase enzyme sample may be derived for a mammal, such as a mouse, rat, guinea pig, dog, cat, horse, pig, non-human primate, or human. Samples may be used with or without further processing. In some instances a sample may be sterilized, homogenized, diluted, disassociated, or processed to isolate particular cell types or cellular components, such as lysosomes. Methods thereof are well known to those of skill in the art.

Glucocerebrosidase enzyme samples may be intermediates in a process of therapeutic production, including without limitation purified glucocerebrosidase enzyme not yet processed into a therapeutic form.

Physiologically Relevant Substrates of Glucocerebrosidase Enzyme

The term "physiologically relevant substrate" can refer to any substrate susceptible to hydrolysis catalyzed by glucocerebrosidase. Such physiologically relevant substrates can be representative of one or more substrates that accumulate in patients suffering from a glucocerebrosidase deficiency, such as Gaucher disease. In particular instances, a physiologically relevant substrate contains a hydrolytic moiety similar to that found in a biological target substrate. Thus, in particular embodiments, a physiologically relevant substrate can include one or more substrates that accumulate in patients suffering from glucocerebrosidase deficiency, such as Gaucher disease. In some embodiments, a physiologically relevant substrate suitable for the present invention is glucosylceramide. Glucocerebrosidase is known to catalyze the hydrolysis of glucosylceramide to ceramide and glucose at the glucosidic linkage of glucosylceramide. Glucosylceramide typically accumulates abnormally in various tissues of patients suffering from Gaucher disease, where glucocerebrosidase is absent or nonfunctional. In some embodiments, a physiologically relevant substrate suitable for the present invention can be a compound that includes a glucosylceramide moiety.

In some embodiments, a substrate useful in accordance with the present invention is of Formula I:

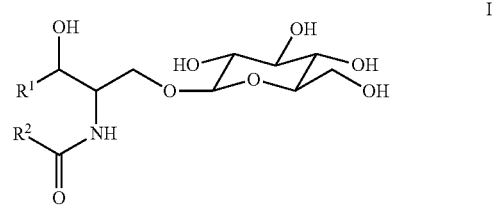

wherein:
$R^1$ is a $C_{4-30}$ straight or branched, saturated or unsaturated, hydrocarbon chain optionally substituted with a detectable moiety or one or more hydroxyl groups; and
$R^2$ is a $C_{4-30}$ straight or branched, saturated or unsaturated, hydrocarbon chain optionally substituted with a detectable moiety or one or more hydroxyl groups.

In some embodiments, $R^1$ is a $C_{6-26}$ straight or branched, saturated or unsaturated, hydrocarbon chain optionally substituted with one or more hydroxyl groups. In some embodiments, $R^1$ is a $C_{8-22}$ straight or branched, saturated or unsaturated, hydrocarbon chain optionally substituted with one or more hydroxyl groups. In some embodiments, $R^1$ is a $C_{10-20}$ straight or branched, saturated or unsaturated, hydrocarbon chain optionally substituted with one or more hydroxyl groups. In some embodiments, $R^1$ is a $C_{12-18}$ straight or branched, saturated or unsaturated, hydrocarbon chain optionally substituted with one or more hydroxyl groups. In some embodiments, $R^1$ is a $C_{14-16}$ straight or branched, saturated or unsaturated, hydrocarbon chain optionally substituted with one or more hydroxyl groups.

In some embodiments, $R^1$ is a $C_{4-30}$ straight hydrocarbon chain optionally having one or two units of unsaturation, optionally substituted with one or more hydroxyl groups. In some embodiments, $R^1$ is a $C_{6-26}$ straight hydrocarbon chain optionally having one or two units of unsaturation, optionally substituted with one or more hydroxyl groups. In some embodiments, $R^1$ is a $C_{8-22}$ straight hydrocarbon chain optionally having one or two units of unsaturation, optionally substituted with one or more hydroxyl groups. In some embodiments, $R^1$ is a $C_{10-20}$ straight hydrocarbon chain optionally having one or two units of unsaturation, optionally substituted with one or more hydroxyl groups. In some embodiments, $R^1$ is a $C_{12-18}$ straight hydrocarbon chain optionally having one or two units of unsaturation, optionally substituted with one or more hydroxyl groups. In some embodiments, $R^1$ is a $C_{14-16}$ straight hydrocarbon chain optionally having one or two units of unsaturation, optionally substituted with one or more hydroxyl groups.

In some embodiments, $R^1$ is a $C_{10-20}$ straight hydrocarbon chain having one unit of unsaturation. In some embodiments, $R^1$ is a $C_{12-18}$ straight hydrocarbon chain having one unit of unsaturation. In some embodiments, $R^1$ is a $C_{14-16}$ straight hydrocarbon chain having one unit of unsaturation. In some embodiments, $R^1$ is a $C_{10}$, $C_{11}$, $C_{12}$, $C_{13}$, $C_{14}$, $C_{15}$, $C_{16}$, $C_{17}$, $C_{18}$, $C_{19}$, or $C_{20}$ straight hydrocarbon chain having one unit of unsaturation. In some embodiments, $R^1$ is a $C_{15}$ straight hydrocarbon chain having one unit of unsaturation.

In some embodiments, $R^1$ is

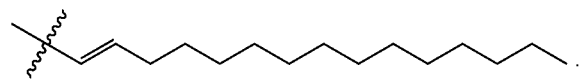 [SMILES: */C=C/CCCCCCCCCCCCC]

In some embodiments, $R^2$ is a $C_{6-26}$ straight or branched, saturated or unsaturated, hydrocarbon chain optionally substituted with one or more hydroxyl groups. In some embodiments, $R^2$ is a $C_{10-24}$ straight or branched, saturated or unsaturated, hydrocarbon chain optionally substituted with one or more hydroxyl groups. In some embodiments, $R^2$ is a $C_{12-22}$ straight or branched, saturated or unsaturated, hydrocarbon chain optionally substituted with one or more hydroxyl groups. In some embodiments, $R^2$ is a $C_{14-20}$ straight or branched, saturated or unsaturated, hydrocarbon chain optionally substituted with one or more hydroxyl groups. In some embodiments, $R^2$ is a $C_{16-18}$ straight or branched, saturated or unsaturated, hydrocarbon chain optionally substituted with one or more hydroxyl groups.

In some embodiments, $R^2$ is a $C_{4-30}$ straight hydrocarbon chain optionally having one or two units of unsaturation, optionally substituted with one or more hydroxyl groups. In some embodiments, $R^2$ is a $C_{6-26}$ straight hydrocarbon chain optionally having one or two units of unsaturation, optionally substituted with one or more hydroxyl groups. In some embodiments, $R^2$ is a $C_{10-24}$ straight hydrocarbon chain optionally having one or two units of unsaturation, optionally substituted with one or more hydroxyl groups. In some embodiments, $R^2$ is a $C_{12-22}$ straight hydrocarbon chain optionally having one or two units of unsaturation, optionally substituted with one or more hydroxyl groups. In some embodiments, $R^2$ is a $C_{14-20}$ straight hydrocarbon chain optionally having one or two units of unsaturation, optionally substituted with one or more hydroxyl groups. In some embodiments, $R^2$ is a $C_{16-18}$ straight hydrocarbon chain optionally having one or two units of unsaturation, optionally substituted with one or more hydroxyl groups.

In some embodiments, $R^2$ is a $C_{10-20}$ straight hydrocarbon chain having one unit of unsaturation. In some embodiments, $R^2$ is a $C_{12-18}$ straight hydrocarbon chain having one unit of unsaturation. In some embodiments, $R^2$ is a $C_{14-16}$ straight hydrocarbon chain having one unit of unsaturation. In some embodiments, $R^2$ is a $C_{10}$, $C_{11}$, $C_{12}$, $C_{13}$, $C_{14}$, $C_{15}$, $C_{16}$, $C_{17}$, $C_{18}$, $C_{19}$, or $C_{20}$ straight hydrocarbon chain having one unit of unsaturation. In some embodiments, $R^2$ is a $C_{17}$ straight hydrocarbon chain having one unit of unsaturation.

In some embodiments, $R^2$ is

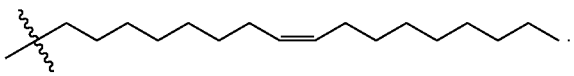 [SMILES: *CCCCCCC/C=C\CCCCCCCC]

In some embodiments of provided methods, a compound of formula I is a compound of formula I-a:

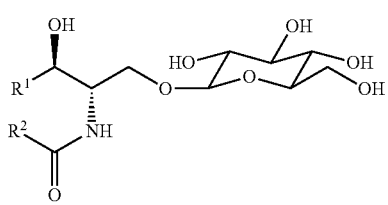

wherein each of $R^1$ and $R^2$ is as defined above and described in classes and subclasses herein, both singly and in combination.

In some embodiments of provided methods, a compound of formula I is a compound of formula II:

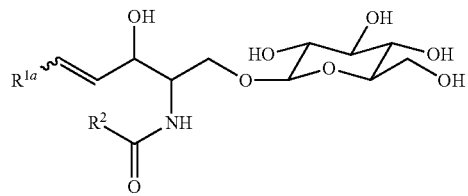

wherein $R^2$ is as defined above and described in classes and subclasses herein, ⁓ refers to either cis or trans double bond stereochemistry, or a mixture thereof; and $R^{1a}$ is a $C_{2-28}$ straight or branched, saturated or unsaturated, hydrocarbon chain optionally substituted with a detectable moiety or one or more hydroxyl groups.

In some embodiments, $R^{1a}$ is a $C_{4-24}$ straight or branched, saturated or unsaturated, hydrocarbon chain optionally substituted with one or more hydroxyl groups. In some embodiments, $R^{1a}$ is a $C_{6-20}$ straight or branched, saturated or unsaturated, hydrocarbon chain optionally substituted with one or more hydroxyl groups. In some embodiments, $R^{1a}$ is a $C_{8-18}$ straight or branched, saturated or unsaturated, hydrocarbon chain optionally substituted with one or more hydroxyl groups. In some embodiments, $R^{1a}$ is a $C_{10-16}$ straight or branched, saturated or unsaturated, hydrocarbon chain optionally substituted with one or more hydroxyl groups. In some embodiments, $R^{1a}$ is a $C_{12-14}$ straight or branched, saturated or unsaturated, hydrocarbon chain optionally substituted with one or more hydroxyl groups.

In some embodiments, $R^{1a}$ is a $C_{2-28}$ straight hydrocarbon chain optionally having one unit of unsaturation, optionally substituted with one or more hydroxyl groups. In some embodiments, $R^{1a}$ is a $C_{4-24}$ straight hydrocarbon chain optionally having one unit of unsaturation, optionally substituted with one or more hydroxyl groups. In some embodiments, $R^{1a}$ is a $C_{6-20}$ straight hydrocarbon chain optionally having one unit of unsaturation, optionally substituted with one or more hydroxyl groups. In some embodiments, $R^{1a}$ is a $C_{8-18}$ straight hydrocarbon chain optionally having one unit of unsaturation, optionally substituted with one or more hydroxyl groups. In some embodiments, $R^{1a}$ is a $C_{10-16}$ straight hydrocarbon chain optionally having one unit of unsaturation, optionally substituted with one or more hydroxyl groups. In some embodiments, $R^{1a}$ is a $C_{12-14}$ straight hydrocarbon chain optionally having one unit of unsaturation, optionally substituted with one or more hydroxyl groups.

In some embodiments, $R^{1a}$ is a $C_{8-18}$ straight, saturated hydrocarbon chain having one unit of unsaturation. In some embodiments, $R^{1a}$ is a $C_{10-16}$ straight, saturated hydrocarbon chain having one unit of unsaturation. In some embodiments, $R^{1a}$ is a $C_{12-14}$ straight, saturated hydrocarbon chain having one unit of unsaturation. In some embodiments, $R^{1a}$ is a $C_8$, $C_9$, $C_{10}$, $C_{11}$, $C_{12}$, $C_{13}$, $C_{14}$, $C_{15}$, $C_{16}$, $C_{17}$, or $C_{18}$ straight, saturated hydrocarbon chain having one unit of unsaturation. In some embodiments, $R^{1a}$ is a $C_{13}$ straight, saturated hydrocarbon chain having one unit of unsaturation.

In some embodiments, $R^{1a}$ is

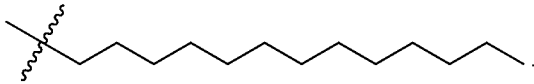 [SMILES: *CCCCCCCCCCCCC]

In combination with any of the embodiments described herein, one or both of $R^1$ and $R^2$ independently comprises a detectable moiety.

In some embodiments of provided methods, a compound of formula I is a compound of formula II-a:

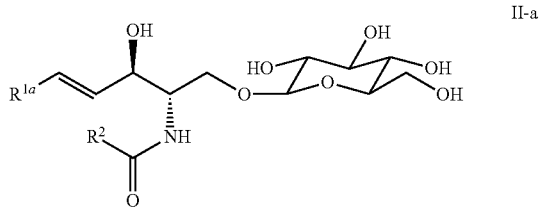

wherein each of $R^{1a}$ and $R^2$ is as defined above and described in classes and subclasses herein, both singly and in combination.

In some embodiments of provided methods, a compound of formula I is:

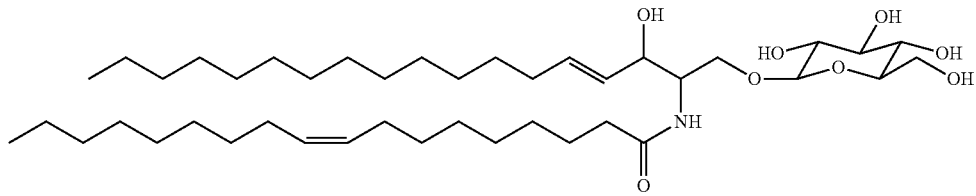 [SMILES: CCCCCCCC/C=C\CCCCCCCC(=O)NC(COC1OC(CO)C(O)C(O)C1O)C(O)/C=C/CCCCCCCCCCCCC]

In some embodiments of provided methods, a compound of formula I is:

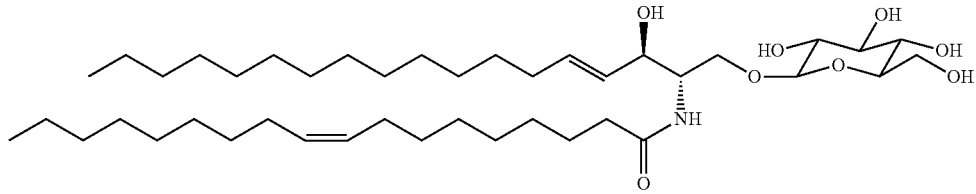 [SMILES: CCCCCCCC/C=C\CCCCCCCC(=O)N[C@@H](COC1OC(CO)C(O)C(O)C1O)[C@H](O)/C=C/CCCCCCCCCCCCC]

Additional substrates suitable for the present invention may include, but are not limited to, aryl β-D-glucosides such as 4-methylumbelliferyl β-D-glucoside (MUG1c) and p-nitrophenyl β-D-glucoside, fluorogenic substrates such as arylglucoside (4-methylumbelliferyl-β-D-glucopyranoside), 2,3-di-O-tetradecyl-1-O-(β-D-glucopyranosyl-sn-glycerol (2,3-di-14:0-β-Glc-DAG), β-D-glucosides such as 4-methylumbelliferyl β-glucoside and p-nitrophenyl β-D-glucoside, 2-Hexadecanoylamino-4-nitrophenyl β-D-glucopyranoside, aryl glycosides (e.g. 4-methylumbelliferyl β-D-glucopyranoside, p-nitrophenyl beta-D-glucopyranoside), and one or more substrates selected from amongst naturally occurring glycosides such as L-picein, dhurrin and glucocheirolin, analogs of glucosyldiacyl (or dialkyl) glycerols and glucosylceramide such as 2,3-di-O-tetradecyl-1-O-(β-D-glucopyranosyl)-sn-glycerol (2,3-di-14:0-,J-Gle-DAG).

In addition, glucocerebrosidase is capable of catalyzing transglucosylation between glucosylceramide and n-alkanols, a transglucosylation reaction between glucosylceramide and retinol, a transglucosylation reaction in vitro between glucosylceramide and alcohols such as n-pentanol and retinol. The glucocerebrosidase-catalyzed transglucosylation reaction with retinol can result in the synthesis of a novel glucoside, retinyl β-D-glucoside. Various substrates may be designed based on transglucosylation reactions described herein.

In various embodiments, physiologically relevant substrates are substrates that are sphingolipid-like, including glucose attached to two carbon-based chains.

Labeled and Unlabeled Substrates

In certain embodiments of the present invention, a physiologically relevant substrate can be labeled with a detectable moiety as defined above in manner that enables the qualitative or quantitative determination of one or more kinetic parameters of glucocerebrosidase enzyme. In other instances, the glucocerebrosidase substrate is not labeled.

Those of skill in the art will appreciate that a wide variety of labels may used in conjunction with the compositions and methods of the present invention. Moreover, suitable methods of detection for the same are also known in the art. In particular instances, a label may be positioned at either R1 or R2. In particular instances, a label may be positioned at R2.

In some instances, a glucocerebrosidase substrate of the present invention is C18:1 glucosylceramide.

Fluorogenic enzyme substrates are known in the art for the measurement of glucocerebrosidase activity. The most commonly used include 4-methylumbelliferyl-β-D-glucopyranoside (4MU-β-glc), p-nitrophenyl-β-D-glucopyranoside, resorufin-β-D-glucopyranoside (res-β-glc), bodipy-glucosylceramide, N-[11-(dipyrromethenboron difluoride) undecanoyl]-D-glucosyl-β1-1'-D-erythrosphingosine, and di-β-D-glucopyranoside (flu-β-glc).

In some embodiments, a detectable moiety is selected from the group consisting of 2-aminobenzoic acid, 2-amino acridone, hydroxy- and amino-substituted coumarins and fluorescent 7-hydroxy coumarin compounds with substitutions in the 4 position having a length greater than one carbon atom, which may be related to 4-MU, and 4-MU. Some examples of such 7-hydroxy coumarins include phosphate, ester and ether derivatives of 7-hydroxy-4-methylcoumarin (β-methylumbelliferone), typified by 4-methylumbelliferyl phosphate (MUP), 7-hydroxy-4-methylcoumarin, 6,8-Difluoro-7-hydroxy-4-methylcoumarin (DiFMU), and the 7-hydroxycoumarin fluorophorethe phosphate ester of 6,8-difluoro-7-hydroxy- 4-methylcoumarin (DiFMUP). In some embodiments, a detectable moiety is selected from the group consisting of 4-methylumbelliferyl-β-D-glucuronide (MUG), 4-methylumbelliferyl-β-D-glucoside (MBGL), 4-methylumbelliferyl-β-d-galactoside (MBGA), 4-methylumbelliferyl-alpha-D-galactoside (MAGA), and 4-methylumbelliferyl-alpha-D-glucoside (MAGL). Other non-limiting examples of a detectable moiety include nitrophenol substrates such as o-nitro-phenol-β-D galactopyranoside (ONPG), p-nitrophenol-N-acetyl-β-D-glucosaminide (NAG), p-nitrophenol-alpha-D-fucopyranoside (AFU), o-nitrophenol-alpha-D-glucopyranoside (AGLU), and PO4-(alkaline phosphatase), as well as naphthylamide substrates such as arginine β-naphthylamide (ARG), proline-β-naphthylamide (PRO), pyrrolidonyl-β-naphthylamide (PYR), Na-Benzoyl-DL-arginine-β-naphtylamide-"trypsin" (TRY), N-Glutaryl-Gly-Gly-Phe-β-naphthylamide-"chymotrypsin" (CHY), and Leucyl glycine β naphthylamide (LGY). Still other detectable groups that may be used include BODIPY, p-nitrophenyl, Resorufin, naphthyl labels, 1,9-dimethylmethylene blue (DMMB), toluidine blue, Alcian blue, and related labels.

In certain embodiments, a detectable moiety is a fluorescent label. In some embodiments, a fluorescent label is or comprises a nitrobenzoxadiazole NBD fluorophore, such as NBD-X. In particular instances, analysis of a substrate including NBD will require separation of NBD-substrate from the NBD-product produced by enzyme catalysis. In some embodiments, a detectable moiety is detectable via chemiluminescence or ultraviolet/visible absorbance spectroscopy.

A wide variety of labels may be appropriate to the compositions and methods of the present invention. In certain embodiments the label is not fluorescent and is detectable by other means such as radioactivity analysis. In some instances, the substrate is not labeled and is detectable by other means, for example by pulsed amperometric detection of the carbohydrate leaving group, conductivity detection of sulfate leaving group, or by mass spectrometry.

In certain embodiments of the present invention, reaction products are detectable in the absence of a detectable moiety on the reaction substrate. In various embodiments, the reaction product that is detected is glucose. Many methods of detecting glucose are known in the art, including methods that utilize glucose oxidase, peroxidase, o-dianiside, ferricyanide, hexokinase, or neocuproine. In some instances, oxidation of glucose produces $H_2O_2$ and the present invention can include the detection of the produced $H_2O_2$. Other methods of detecting glucose employ glucose binding proteins or receptors, such as the polysaccharide-lectin system. Glucose can also be detected using opto-fluidic ring resonator (OFRR), near infrared spectroscopy, infrared spectroscopy, raman spectroscopy, photoacoustic spectroscopy, evanescent wave spectroscopy, the detection of scatter or polarization changes, or by pulsed amperometric detection. Methods known to those of skill in the art include the Flin and Wu method, Somogyi-Shaffer-Hartmann method, Nelson-Somogyi method, Benedict's method, Hankin and Van Slyke method.

Methods for the Determination of Kinetic Parameters

Various methods may be used to determine kinetic parameters of glucocerebrosidase enzyme according to the present invention. For example, various kinetic models are known in the art and can be used to determine kinetic parameters. As used herein, the term "kinetic model" refers to any quantitative description of enzyme reaction rate. Typically, a kinetic model provides a rate equation and/or time course of the reaction. For example, a Michaelis-Menten kinetic model is a common model of a single-substrate reaction. As used herein, kinetic parameters include any parameters indicative of reaction rate and specific activity. Exemplary kinetic parameters with exemplary units for each kinetic parameters include, but are not limited to, $V_{max}$ (µM/min), $K_m$ (µM), $k_{cat}$ (s$^{-1}$). For example, $V_{max}$ represents the maximum rate achieved by the system, at maximum (saturating) substrate concentrations. Typically, enzyme-catalyzed reactions are saturable. Their rate of catalysis does not always show a linear response to increasing substrate. If the initial rate of the reaction is measured over a range of substrate concentrations (denoted as [S]), the reaction rate (v) generally increases as [S] increases. However, as [S] gets higher, the enzyme becomes saturated with substrate and the rate reaches $V_{max}$, the enzyme's maximum rate. $K_m$, also known as the Michaelis constant, is the substrate concentration at which the reaction rate is half of $V_{max}$. Specific activity is typically defined as the amount of substrate the enzyme converts (reactions catalyzed), per mg protein in the enzyme preparation, per unit of time. The range of any particular parameter as determined, e.g., by a method of the present invention or by a method including a composition of the present invention, will vary depending upon numerous factors and conditions.

In certain embodiments of the present invention, glucocerebrosidase enzyme kinetic parameters are determined by incubating a glucocerebrosidase enzyme sample with a desired amount of substrate under conditions that permit glucocerebrosidase to catalyze hydrolysis of the substrate and analyze the formation of one or more products. Thus, various assay reactions can occur under conditions that permit glucocerebrosidase-catalyzed hydrolysis of a physiologically relevant substrate. In some instances, the reaction mixture can be separated by chromatography. After chromatography, a detection unit can be used to measure the product signal. In some instances, a product will include a detectable label. In various embodiments, it is critical that the catalytic reaction is in the initial rate region (where the product formation or substrate depletion is linear with respect to time); in such embodiments, only under initial rate conditions is the Michaelis-Menten model valid for determining kinetic parameters. Therefore, in such embodiments, experimental conditions must be selected to ensure that initial rates are measured, and to ensure that all other Michaelis-Menten model assumptions are met.

In any embodiment, the substrate may be present in a mixture or solution, e.g., in mixture or solution with a liquid such as a buffer or a solution in water. The mixture or solution may be an aqueous mixture or solution. A wide variety of reagents for use in mixtures or solutions are known in the art. In various embodiments, the substrate is present in a mixture or solution that includes lipids. The lipids may be of a single species or a plurality of species.

In some instances, a substrate may be sonicated prior to use or prior to dilution, including when present in a mixture or solution. For instance, a substrate may be sonicated at 60% AMPL for 5 minutes. In particular instances, a buffer for use with a substrate may be sonicated. In certain instances, a buffer for use with a substrate may be sonicated at 60% AMPL for 5 minutes. In some instances, a sonicated buffer is added to a sonicated or non-sonicated substrate. In further instances, after combination of a sonicated buffer to a substrate, the mixture is further sonicated, e.g., at 60% AMPL for 5 minutes. Substrate or product for any or all experimental assay reactions, controls, or standards may be similarly sonicated. In various embodiments, sonication disperses substrate into micelles. In any of the various embodiments in which a substrate is sonicated, e.g., prior to use or prior to dilution, including when present in a mixture or solution, the sonication may be, e.g., at 1% to 100% AMPL, e.g., 1%, 5%, 10%, 20%, 30%, 40%, 50%, 60%, 70%, 80%, 90%, or 100% AMPL, or any range therebetween. In any of the various embodiments in which a substrate is sonicated, e.g., prior to use or prior to dilution, including when present in a mixture or solution, the sonication may be, e.g., for 10 seconds to 2 hours or more, e.g., 10 seconds, 20 seconds, 30 seconds, 1 minute, 2 minutes, 3 minutes, 4 minutes, 5 minutes, 6 minutes, 7 minutes, 8 minutes, 9 minutes, 10 minutes, 20 minutes, 30 minutes, 1 hour, 2 hours, or more, or any range therebetween. For example, sonication may be for about 0 to 120 minutes (e.g., about 10 seconds to 60 minutes, 10 seconds to 30 minutes, 10 seconds to 20 minutes, 1 minute to 20 minutes, 1 minute to 10 minutes, 3 minutes to 10 minutes, 3 minutes to 8 minutes, 4 minutes to 6 minutes, or 3 minutes to 20 minutes).

A reaction of the present invention may be prepared by combining an amount of enzyme with an amount of substrate in a buffer sufficient to allow the enzyme to act upon the substrate. In some instances, the amount of enzyme in a reaction of the present invention is 0.0001 ng/μL or more, e.g., 0.0001 ng/μL, 0.0005 ng/μL, 0.001 ng/μL, 0.005 ng/μL, 0.01 ng/μL, 0.02 ng/μL, 0.03 ng/μL, 0.04 ng/μL, 0.05 ng/μL, 0.06 ng/μL, 0.07 ng/μL, 0.08 ng/μL, 0.09 ng/μL, 0.1 ng/μL, 0.5 ng/μL, 1 ng/μL, 2 ng/μL, 3 ng/μL, 4 ng/μL, 5 ng/μL, 6 ng/μL, 7 ng/μL, 8 ng/μL, 9 ng/μL, 0.01 mg/ml, 0.05 mg/ml, 0.1 mg/ml, 0.5 mg/ml, 1 mg/ml, 2 mg/mL, 3 mg/mL, 4 mg/mL, 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, or more, or any range therebetween. The enzyme concentration may also be less than 0.0001 ng/mL. Those of skill in the art will appreciate that the concentration of a molecule, when provided as a mass per unit volume, is equivalent to providing that molecules molarity when the mass of the molecule is known. In some instances, the amount of enzyme in a sample is unknown. For instance, in some instances a sample may be tested based on the mass or volume of starting sample rather than any determination of the composition of the sample with respect to enzyme.

In some instances, the amount of substrate in a reaction of the present invention is 0.1 μM or more, e.g., 0.1 μM, 0.2 μM, 0.3 μM, 0.4 μM, 0.5 μM, 1 μM, 2 μM, 3 μM, 4 μM, 5 μM, 10 μM, 15 μM, 20 μM, 25 μM, 30 μM, 35 μM, 40 μM, 45 μM, 50 μM, 100 μM, 200 μM, 300 μM, 400 μM, 500 μM, 1 mM, 2 mM, 3 mM, 4 mM, 5 mM, 10 mM or higher, or any range therebetween. The substrate concentration may also be less than 0.1 μM.

In some instances, the amount of substrate in a reaction of the present invention is 1 ng/mL or more, e.g., 1 ng/mL, 2 ng/mL, 3 ng/mL, 4 ng/mL, 5 ng/mL, 10 ng/mL, 20 ng/mL, 30 ng/mL, 40 ng/mL, 50 ng/mL, 100 ng/mL, 1 μg/mL, 2 μg/mL, 3 μg/mL, 4 μg/mL, 5 μg/mL, 6 μg/mL, 7 μg/mL, 8 μg/mL, 9 μg/mL, or 10 μg/mL, or more substrate, or any range therebetween. The substrate a may also be less than 1 ng/mL.

The ratio of enzyme to substrate in an experimental or control reaction of the present invention may be, in some instances, 0.001 ng enzyme to 0.1 ng substrate; 0.005 ng enzyme to 0.2 ng substrate; 0.01 ng enzyme to 0.3 ng substrate; 0.05 ng enzyme to 0.4 ng substrate; 0.1 ng enzyme to 0.5 ng substrate; 0.2 ng enzyme to 1 ng substrate; 0.3 ng enzyme to 2 ng substrate; 0.4 ng enzyme to 3 ng substrate; 0.5 ng enzyme to 4 ng substrate; 0.6 ng enzyme to 5 ng substrate; 0.7 ng enzyme to 10 ng substrate; 0.8 ng enzyme to 100 ng substrate; 0.9 ng enzyme to 1 μg substrate; 1 ng enzyme to 10 μg substrate; 5 ng enzyme to 20 μg substrate; 10 ng enzyme to 30 μg substrate; 20 ng enzyme to 40 μg substrate; 30 ng enzyme to 50 μg substrate; 40 ng enzyme to 60 μg substrate; 50 ng enzyme to 70 μg substrate; 100 ng enzyme to 80 μg substrate; 500 ng enzyme to 90 μg substrate; 1 μg enzyme to 100 μg substrate; 0.001 ng enzyme to 100 μg substrate; 0.005 ng enzyme to 90 μg substrate; 0.01 ng enzyme to 80 μg substrate; 0.05 ng enzyme to 70 μg substrate; 0.1 ng enzyme to 60 μg substrate; 0.2 ng enzyme to 50 μg substrate; 0.3 ng enzyme to 40 μg substrate; 0.4 ng enzyme to 30 μg substrate; 0.5 ng enzyme to 20 μg substrate; 0.6 ng enzyme to 10 μg substrate; 0.7 ng enzyme to 1 μg substrate; 0.8 ng enzyme to 100 ng substrate; 0.9 ng enzyme to 10 ng substrate; 1 ng enzyme to 5 ng substrate; 5 ng enzyme to 4 ng substrate; 10 ng enzyme to 3 ng substrate; 20 ng enzyme to 2 ng substrate; 30 ng enzyme to 1 ng substrate; 40 ng enzyme to 0.5 ng substrate; 50 ng enzyme to 0.4 ng substrate; 100 ng enzyme to 0.3 ng substrate; 500 ng enzyme to 0.2 ng substrate; or 1 μg enzyme to 0.1 ng substrate, or any range therebetween. In certain embodiments, the concentration of substrate is significantly greater than the concentration of enzyme. In such embodiments, a concentration of substrate greater than the concentration of enzyme can facilitate application of the Micahelis-Menten model.

In various embodiments, a reaction of the present invention can include lipids. In particular embodiments, a reaction of the present invention can include taurocholic acid. In certain embodiments, a reaction of the present invention can include oleic acid. In some embodiments, a reaction of the present invention can include a combination of taurocholic acid and oleic acid. In various instances including taurocholic acid, the concentration of taurocholic acid in a reaction will be from 0.5 to 100 mM or more taurocholic acid, e.g., 0.5 mM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 20 mM, 30 mM, 40 mM, 50 mM 75 mM, 100 mM, or more, or any range therebetween. For example, taurocholic acid may be included at a concentration of about 0.5 to 100 mM (e.g., about 0.5 to 50 mM, 0.5 to 40 mM, 0.5 to 30 M, 0.5 to 25 mM, 0.5 to 15 mM, 0.5 to 10, 1 to 9 mM, 2 to 8 mM, or 5 to 8 mM). In particular embodiments, the concentration of taurocholic acid in a reaction will be between 2 mM and 10 mM. In still more particular embodiments, the concentration of taurocholic acid will be between 5 mM and 8 mM or 5 mM and 6.5 mM. In some instances, a concentration of 6.5 mM taurocholic acid is included in one or more reactions of the present invention. In any embodiments including taurocholic acid in a reaction, the reaction may also include oleic acid. In embodiments in which a reaction of the present invention includes oleic acid, the amount of oleic acid in the composition can be represented as a percentage by weight, percentage by volume, or mole percentage. In any of these cases, the percentage of oleic acid can be equal to or less than 5%, e.g., 0.001% or less to 5%. For instance, the percentage of oleic acid (for example, w/w or v/v) in a reaction of the present invention can be 5%, 4%, 3%, 2%, 1%, 0.9%, 0.8%, 0.7%, 0.6%, 0.5%, 0.4%, 0.3%, 0.2%, 0.1%, 0.09%%, 0.08%, 0.07%, 0.06%, 0.05%, 0.04%, 0.03%, 0.02%, 0.01% or less, or any range therebetween. For example, the oleic acid may be included at a percentage from 0 to 5 percent (e.g., about 0.001% to 5%, 0.001% to 3%, 0.001% to 1%, 0.001% to 0.5%, 0.001% to 0.05%, 0.01% to 0.05%, 0.01% to 0.5%, 0.05% to 0.5%, or 1% to 5%. In particular examples, the percentage of oleic acid between 0.01% and 1%, between 0.1% and 0.5%, or between 0.1% and 0.3%. In particular examples, the percentage of oleic acid will be about 0.2%. In particular examples, the percentage of oleic acid will be less than 0.05%, between 0.01% and 0.05%, or between 0.01% and 0.1%. In any embodiments including oleic acid in a reaction, the reaction may also include taurocholic acid.

Any embodiments including one or both, or neither, of taurocholic acid and oleic acid may include one or more other lipids, e.g., at concentrations appropriate for use in reactions of the present invention. Such other or additional lipids may be lipids known in the art to have similar properties to one or both of taurocholic acid or oleic acid. For instance, a reaction may include oleic acid and a lipid recognized in the art as similar to taurocholic acid, taurocholic acid and a lipid recognized in the art as similar to oleic acid, or one or both of a lipid recognized in the art as similar to taurocholic acid and a lipid recognized in the art as similar to oleic acid. It will be clear to those of skill in the art that, typically, all reactions of given trial, sequence of reactions, group of reactions, or experiment will include the same or similar reaction conditions with the optional exception of one or a small number of elements.

Upon mixing of substrate and enzyme, the assay reaction may be incubated for a period sufficient to allow the enzyme to act upon the substrate in a detectable manner, e.g., while maintaining the product formation in the initial rate region. Controls and standards, when present, should be incubated in kind.

In certain instances, the reaction is incubated at a temperature between 1° C. and 99° C., such as 10° C., 15° C., 20° C., 25° C., 30° C., 35° C., 40° C., 45° C., or 50° C., or any range therebetween. In particular instances, the reaction may be incubated at a temperature between 15° C. and 45° C., e.g., a temperature between 20° C. and 37 ° C., 25° C. and 30° C., a temperature between 35° C. and 40° C., at 20 ° C., at room temperature, at 30 ° C., at 37° C., a temperature between 32° C. and 42° C., e.g., 32° C., 33° C., 34° C., 35° C., 36° C., 37° C., 38° C., 39° C., 40° C., 41° C., or 42° C.

In some instances the pH used in the present assay may be acidic. The pH may be acidic for one or more or all of control reactions, experimental reactions, or standard curve reactions. For instance, assay reactions may be at a pH of 1 to 6.5, such as 1, 1.5, 2, 2.5, 3, 3.5, 4, 4.5, 5, 5.5, 6, or 6.5, or any range therebetween. In other instances one or more assay reactions may have a neutral or basic pH, such as a pH of 6.5 to 7.5 or a pH of 7.5 to 14.

Assay reactions may further include BSA. For instance, assay reactions may include BSA at a concentration of 0.001 to 1 mg/mL, e.g., 0.001, 0.005, 0.01, 0.05, 0.1, 0.2, 0.3, 0.4, 0.5, 0.6, 0.7, 0.8, 0.9, or 1 mg/mL, or any range therebetween. In particular instances, assay reactions may include between 0 and 0.4 mg/mL BSA. Various kinetic parameters as determined by such assays may depend in part upon the concentration of BSA.

The length of the incubation period may be from 10 seconds to 2 weeks or longer, such as 10 seconds, 30 seconds, 1 minute, 5 minutes, 10 minutes, 20 minutes, 30 minutes, 40 minutes, 50 minutes, 1 hour, 2 hours, 3 hours, 4 hours, 5 hours, 6 hours, 12 hours, 1 day, 2, days, 3 days, 4 days, 5 days, 6 days, 1 week, 2 weeks, or longer. The incubation temperature may modulate the appropriate period of time for the incubation of the reaction. In various embodiments, the length of the incubation period is within the initial rate region.

Following the incubation period, the enzymatic reaction may be quenched through application of quenching treatment, such as addition of a quenching agent. An exemplary quenching treatment may be a heat treatment. A reaction of the present invention may be stopped by incubating the reaction, e.g., at a high temperature for a period of time. For example, a reaction may be heat inactivated by incubation at a temperature of 60° C., 65° C., 70° C., 75° C., 80° C., 85° C., 90° C., 95° C., or 99° C., or any range therebetween. The length of this heat-inactivating incubation may be, e.g., 10 second or longer, such as 10 seconds, 30 seconds, 1 minute, 5 minutes, 10 minutes, 20 minutes, 30 minutes, 40 minutes, 50 minutes, 1 hour, 2 hours, 3 hours, 4 hours, 5 hours, 6 hours, 12 hours, 1 day, 2, days, 3 days, 4 days, 5 days, 6 days, 1 week, 2 weeks, or longer. The incubation temperature may modulate the appropriate period of time for the incubation of the reaction. Other methods of enzyme activation are known in the art. For instance, in some instances, an enzyme reaction may be stopped by the addition of acetonitrile or similar agents. Acetonitrile may be provided in a pure form or in a diluted form, e.g., a dilution that is 95%, 90%, 85%, 80%, 75%, 70%, 65%, 60%, 55%, 50%, 45%, 40%, 35% or 30% or less acetonitrile by volume. In particular instances, the acetonitrile may be diluted in water. Other quenching agents or treatments that may be used alternatively or in combination with acetonitrile or heat treatment, include, without limitation, methanol, ethanol, isopropyl alcohol, acetone, or the like are, and organic solvents in general.

The assay of the present invention may occur in wells appropriate to the volume of the assay reaction. The reaction volume may be, for example, 1 μL, 2 μL, 3 μL, 4 μL, 5 μL, 10 μL, 20 μL, 30 μL, 40 μL, 50 μL, 100 μL, 200 μL, 300 μL, 400 μL, 500 μL, 1 mL, 2 mL, 3 mL, 4 mL, 5 mL, 10 mL, or more, or any range therebetween.

The present invention includes the detection of one or more reaction products produced by the incubation of glucocerebrosidase enzyme with a suitable substrate. In particular instances, the present invention includes the detection of glucose. Particular reaction products such as glucose, modified, glucose, detectably labelled glucose, detectably labelled modified glucose, or detectable labels that are not bound to a glucose or modified glucose product may be detected. As will be clear to those of skill in the art, the products that may be detected depends upon the substrate(s) present in the reaction of glucocerebrosidase enzyme with glucocerebrosidase substrate.

The kinetic parameters relating to glucocerebrosidase enzyme can be determined using any of a variety of apparatuses in accordance with the detectable group of the utilized substrate. In particular instances, an assay of the present invention utilizes HPAEC-PAD, such as the Dionex HPAEC-PAD apparatus or the Thermo Scientific HPAEC-PAD apparatus. In such instances, the production of glucose can be analyzed.

Assays to determine the kinetic parameters of glucocerebrosidase enzyme can include control reactions. A control reaction may include substrate from a stock or formulation of substrate previously shown to be acted upon by glucocerebrosidase enzyme, glucocerebrosidase enzyme from a stock or formulation of enzyme previously shown to be capable of acting upon an glucocerebrosidase substrate, or both. An assay to determine kinetic parameters of glucocerebrosidase enzyme can further include wells that include enzyme without substrate, substrate without enzyme, or product without substrate or enzyme. In particular, a standard curve may be generated using samples having a range of known concentrations of product. In certain instances, neither enzyme nor substrate is added to wells used to produce a standard product curve. In some instances, glucose is a reaction product of a glucocerebrosidase enzyme reaction. In particular instances, a series of standard solutions of glucose in varying concentration may be used to produce a standard curve. The standard substrate curve facilitates the correlation of assay readouts with concentrations of product.

In certain instances, a product standard curve provides the basis for determining the concentration of glucose in each assay reaction or aliquots thereof, allowing the rate of product formation to be plotted against substrate concentration. For instance, a glucose product standard curve can be generated by first calculating the average peak area for glucose product standard concentration. Subsequently, a linear regression curve of the average peak area vs. the glucose product standard concentration (μM) can be generated using, e.g., an Empower processing method or Excel. Characteristics of the linear regression curve can be determined, such as $R^2$ values and % CVs. Velocities can be calculated from the product peak areas and the reaction incubation time.

Various embodiments of the present invention utilize concentration ranges of substrate or product, as appropriate, in control, experimental, and standard curve reactions or wells. For instance, a substrate control may be tested across a range of substrate concentrations; a substrate control may be tested across a range of enzyme concentrations; an enzyme control may be tested across a range of enzyme concentrations; an enzyme control may be tested across a range of substrate concentrations; and/or a standard curve may be constructed across a range of product concentrations. Applicable controls may vary depending upon whether the experimental assay reactions include a known substrate and an unknown enzyme, an unknown substrate and a known enzyme, or an unknown substrate and an unknown enzyme. In certain instances, a single assay includes two, three, four, or more replicates of each control, experimental, and standard curve condition.

Methods for the detection of reaction products, such as glucose, can include a chromatographic separation step. In particular instances, the method of separation may include liquid chromatography, thin-layer chromatography, capillary electrophoresis, gas chromatography, or solvent extraction. In some instances, the method of separation may include adsorption chromatography, partition chromatography, normal-phase chromatography, aqueous normal phase chromatography, reverse-phase chromatography, ion exchange chromatography, molecular or size exclusion chromatography, or affinity chromatography. The method of separation may include ultra-performance liquid chromatography (UPLC) or high-performance liquid chromatography (HPLC). HPLC is a method in which a pressurized liquid solvent is contacted with a support, such as a column, the characteristics of which can mediate the separation of molecules present in a mixture. UPLC is a variant of HPLC that may include particle sizes smaller than those used in traditional HPLC methods (e.g., less than 2 um) and may utilize higher pressures than traditional HPLC methods. The method of separation may include high performance anion exchange chromatography (HPAEC). Methods of HPLC, HPAEC, and UPLC are known in the art. A method of separation including chromatography may include a hydrophilic interaction liquid chromatography (HILIC), reversed phase (RP), or charged surface hybrid (CSH) column. In some instances, separation will include one or more steps in which molecules are distinguished based on, e.g., size, polarity, hydrophobicity, charge, fluorescence, radioactivity, spectrophotometric characteristics, spectra, mass, or other characteristics known in the art, or any combination thereof. Separated or unseparated samples may be subjected to a detection step. For instance, fluorescence detection can be useful for sensitive, precise, and/or accurate quantitation at low levels of analyte. In particular instances, the method of detection is pulsed amperometric detection (PAD) or 3D Amperometry. PAD can be used in the detection of underivatized analytes. PAD can involve the application of various potentials to a working electrode over a specific time period. Without being bound to any particular scientific theory, the potential variations can result in oxidizing and reducing conditions on the electrode surface, resulting in oxidation of analytes bound to the working electrode surface. After oxidation, a reduction and reoxidation step can be applied to remove the bound analyte and renew the electrode surface. The variation of the potentials can be performed as a pulse sequence and can typically take less than 1 second, allowing chromatographic data points to be recorded at least every second. Pico- and femtomol sensitivity can be achieved with PAD.

In certain embodiments in which the substrate does not contain a detectable group capable of producing a fluorescent signal, or in embodiments in which the substrate does not contain a detectable group, applicable methods of detection are known in the art. Methods of detection suitable to substrates without a fluorescent detectable group or without any detectable group include, without limitation, conductivity detection, amperometric detection, as well as other methods known in the art and/or described herein.

In instances in which the substrate includes a detectable group capable of producing a fluorescent signal, corresponding methods of detection may include the use of a fluorometer or spectrofluorometer, fluorescence plate reader, fluorescence microscopes, fluorescence scanners, or flow cytometers. The fluorescence of the detectable group is determined for one or more samples or a portion of one or more samples, such as a portion including product that has been separated from substrate. Other methods of detection include detection based on, e.g., size, polarity, hydrophobicity, charge, fluorescence, radioactivity, spectrophotometric characteristics, spectra, mass, or other characteristics known in the art, or any combination thereof.

In certain embodiments, the method includes a separation step and a detection step. In particular instances, chromatographic separation is performed in conjunction with downstream fluorescence detection, conductivity detection, or pulsed amperometric detection. Without limiting the scope of the present invention, specific examples include the use of high performance anion exchange chromatography with pulsed amperometric detection (HPAEC-PAD). In some instances, HPAEC-PAD can separate molecules based upon specific interactions between hydroxyl groups of the molecule and the stationary phase of the column. In some instances of HPAEC-PAD, molecules chromatograph as anionic species and interact with the column based on size, composition, and linkage. High-Performance Anion-Exchange Chromatography is used to separate, e.g., anionic analytes that are either anions in their common form or analytes that can be ionized at high pH values (e.g., carbohydrates at >pH 12). Apparatuses for the performance of HPAEC, PAD, and HPAEC-PAD are available in the art.

In certain instances, assays of the present invention can include gas chromatography. Gas chromatography detectors can include non-selective, selective, specific, concentration dependent, or mass flow dependent detectors. Particular types of detectors can include flame ionization detectors, thermal conductivity detectors, electron capture detectors, and nitrogen phosphorous detectors.

Particular columns for use with any method of the present invention can include an IonPac NG1 Guard Column, 4×35 mm and/or a CarboPac PA10 Analytical Column, e.g., as available from Thermo Scientific.

In certain instances, the invention includes an in-line desalting step. An in-line desalting step can eliminate the need to separately remove lipids from the reaction buffer prior to contacting a sample to an anion exchange analytical column and/or a detection system. In the absence of in-line desalting, methods of the present invention may, in some instances, include alternative methods of desalting that would, in certain cases, increase variability in sample recovery from extraction, introducing variability and, potentially, inaccuracies. Although laboratory procedures are available to address such variability, when present, these procedures can be technically complicated, computationally complicated (e.g., require additional analytical steps or calculations to correct for variation), and/or require additional reagents. Thus, the inclusion of an in-line desalting step or apparatus can simplify data analyses associated with the methods and compositions of the present invention and/or improve accuracy and/or precision of the methods described herein as compared to certain other methods, also included with the scope of the present invention, that do not include in-line desalting.

In certain embodiments, the present invention includes direct injection of an assay reaction or assay reaction product to an apparatus including in-line desalting, e.g., an apparatus including a precolumn and analytical column, e.g., an apparatus including a precolumn directly joined to an analytical column.

In particular instances, an apparatus including in-line desalting can include a reverse phase precolumn and an anion exchange analytical column. The reverse phase precolumn, in some instances, may be utilized to trap lipids. In certain embodiments, the apparatus for in-line desalting includes a reverse phase pre-column joined to an anion exchange analytical column, e.g., directly joined to an anion exchange analytical column.

Any of the above apparatuses may be used in combination with other methods of detection, such as mass spectrometory. For instance, assays of the present invention can include gas chromatograph mass spectrometry (GCMS).

Kinetic parameters relating to glucocerebrosidase enzyme may be determined through the detection of any of one or more reaction products, including glucose but additionally including ceramide as well as other products. One of skill in the art will appreciate that the products available for detection will vary in direction relationship to the substrate of the reaction. Any product produced by the action of a glucocerebrosidase enzyme on a substrate of the present invention may be detected. In particular instances, a product may be modified after the glucocerebrosidase enzyme acts on the substrate but prior to detection, e.g., by chemical or other enzymatic agents present in the reaction. In any embodiment, more than one reaction product may be detected. In certain instances, for example, both glucose and ceramide may be detected.

Although various specific reaction chambers may be referenced throughout the specification, such as centrifuge tubes or 96-well plates, those of skill in the art will appreciate that the reactions of the present invention can occur in any of a wide variety of types of reaction chambers, including, e.g., 384 well plates. Thus, the reaction chamber should not be considered limiting with respect to the scope of the present invention.

Applications

The methods and compositions of the present invention may be employed toward a variety of applications. For instance, methods and compositions of the present invention can be used to monitor manufacturing and purification processes.

In particular, the present invention includes a method for assessing clinically relevant properties of glucocerebrosidase for use in enzyme replacement therapy. For example, kinetic parameters determined according to the present invention may be indicative of enzyme potency and purity; thus, one or more such parameters can be used to as a surrogate of efficacy of glucocerebrosidase for therapeutic use.

The present invention may also be used in quality control during manufacturing process. For instance, commercial production of glucocerebrosidase enzyme therapeutics may include the production of independent, semi-independent, differently or separately treated, or differently or separately handled batches, samples, or aliquots of glucocerebrosidase enzyme or glucocerebrosidase enzyme therapeutic. In such instances, samples of glucocerebrosidase enzyme from diverse sources may be tested to ensure that the glucocerebrosidase enzyme from the various sources possesses consistent or substantially consistent kinetic parameters or kinetic parameters that are sufficiently consistent for therapeutic purposes. In some instances, the kinetic parameters may differ and the production of therapeutic using glucocerebrosidase enzyme from one or more particular sources may be adjusted accordingly with reference to an established standard or therapeutic target.

Further applications relating to the kinetic parameters of glucocerebrosidase enzyme can include the determination of kinetic parameters of stored glucocerebrosidase enzyme. Glucocerebrosidase enzyme can be stored at a variety of temperatures, such as 50° C. or less, e.g., 50° C., 40° C., 30° C., 20° C., 10° C., 0° C., −10° C., −20° C., −30° C., −40° C., −50° C., −100° C. or less, or any range therebetween. Particular storage temperatures may include, e.g., 2° C., 8° C., −65° C., −80° C., or −85° C. Storage times at any temperature may be, e.g., 1 minute to 6 months, e.g., 1 minute, 30 minutes, 1 hour, 2 hours, 4 hours, 6 hours, 8 hours, 10 hours, 12 hours, 1 day, 2 days, 3 days, 4 days, 5 days, 6 days, 1 week, 2 weeks, 3 weeks, 1 month, 2 months, 3 months, 6 months, or longer. Storage times may be longer for stabilized compositions such as stabilized therapeutic compositions. The length of storage may be determined in accordance with the storage temperature or other storage conditions. For instance, in some embodiments, glucocerebrosidase enzyme may be stored at 25° C. for 8 hours or at 2° C. or less for more than 24 hours. Kinetic parameters of glucocerebrosidase enzymes may be determined over the course of storage to ensure sufficient maintenance of enzyme function. For instance, the kinetic parameters of stored glucocerebrosidase enzyme may be sampled at a single interval or at multiple intervals at or at the frequency of 1 minute to 6 months, e.g., 1 minute, 30 minutes, 1 hour, 2 hours, 4 hours, 6 hours, 8 hours, 10 hours, 12 hours, 1 day, 2 days, 3 days, 4 days, 5 days, 6 days, 1 week, 2 weeks, 3 weeks, 1 month, 2 months, 3 months, 6 months, or longer as measured from the beginning of the storage period. Similarly, methods of the present invention may be used to evaluate the kinetic parameters of stored glucocerebrosidase substrate.

In particular embodiments, applications relating to the kinetic parameters of glucocerebrosidase enzyme can include the determination of kinetic parameters of glucocerebrosidase enzyme in a sample having been subjected to conditions that force degradation, induce degradation, or otherwise result in degradation of glucocerebrosidase enzyme. Such conditions can include, e.g., conditions capable of resulting in oxidation by light exposure (photo stress) or other conditions capable of resulting in oxidation. Samples exposed or subjected to conditions capable of forcing or inducing degradation of glucocerebrosidase enzyme, or otherwise resulting in degradation of glucocerebrosidase enzyme, can be assayed by methods and/or compositions of the present invention in order to determine the kinetic parameters of the glucocerebrosidase enzyme at one or more time points, e.g., two time points between which degradation may occur, e.g., a detectable amount of degradation. Degradation may be directly or indirectly reflected in the measured value of one or more kinetic parameters, e.g., $k_{cat}$ and/or $K_m$, as well as other kinetic parameters described herein. In particular examples, a statistically significant decrease in a measured kinetic parameter, e.g., $k_{cat}$, may be correlated to degradation of glucocerebrosidase enzyme. Additional applications of the present invention may include use in methods of diagnostics or personalized medicine. For instance, a sample of glucocerebrosidase enzyme taken from a subject may be used to determine the activity of glucocerebrosidase enzyme from that subject. In such instances, the sample may be used in its initial form or may be further processed, e.g., to purify glucocerebrosidase enzyme or separate distinct forms of glucocerebrosidase enzyme that may be present in the sample. A level of one or more glucocerebrosidase kinetic parameters with respect to a net sample or subset of a sample that falls below a predetermined standard or disease threshold may indicate that treatment with glucocerebrosidase enzyme should be recommended or undertaken. Moreover, the determined kinetic parameters of subject glucocerebrosidase enzyme may be used to determine the dosage or form of glucocerebrosidase enzyme to be recommended, prescribed, or administered as a therapeutic. For instance, where the activity of glucocerebrosidase enzyme taken from a subject having, at risk of having, or having been diagnosed with a glucocerebrosidase enzyme deficiency, such as Gaucher disease, is known, a therapeutic formulation or dosage may be prescribed in a manner corresponding to or compensatory for the degree of deficiency. As such, a therapeutic dosage of glucocerebrosidase enzyme may be provided in a manner that compensates for a glucocerebrosidase enzyme or enzyme activity deficiency in a degree commensurate with deficiency, e.g., as the deficiency relates to a predetermined standard or disease threshold.

In addition, certain studies have encountered difficulty in determining genotype-phenotype correlations between the gene encoding the glucocerebrosidase enzyme, or the protein sequence of the glucocerebrosidase enzyme produced by the gene, and phenotypes associated with glucocerebrosidase enzyme deficiency. For instance, challenges may be encountered in distinguish types of Gaucher disease based on previously available measures of glucocerebrosidase enzyme kinetic parameters. Moreover, in subjects having been therapeutically treated with glucocerebrosidase enzyme, samples of glucocerebrosidase may be taken from the subject and the glucocerebrosidase enzyme kinetic parameters of the glucocerebrosidase enzyme in the sample may be determined according to the present invention in order to determine the efficacy or stability of treatment and related treatment parameters. The presently claimed compositions and methods may provide greater diagnostic capacity for these and related applications.

The compositions and methods of the present invention can also be used to identify molecules other than glucocerebrosidase enzyme and glucocerebrosidase substrate that may be used to modulate glucocerebrosidase enzyme kinetic parameters. For instance, several therapeutic approaches have emerged in which pharmacological chaperone therapy or activity enhancement of mutant enzyme have been used in the treatment of Gaucher disease. Pharmacological chaperones are small molecules that can bind to mutant proteins and assist in their correct folding, maturation, and trafficking. Examples include isofagomine, an iminosugar analog, and related chaperones. In addition, small molecule activators capable of enhancing the kinetic parameters of native or synthetic glucocerebrosidase enzyme, including functional glucocerebrosidase enzyme as well as non-functional or par-functional glucocerebrosidase enzyme, as may be present in a subject (e.g., a subject having Gaucher disease). Moreover, studies have suggested that the causes of Gaucher disease may include factors beyond the characteristics of a subject's glucocerebrosidase enzyme alone, and additional factors may be incorporated into an assay of the present invention to identify compounds of therapeutic or research value that may contribute to glucocerebrosidase enzyme kinetic parameters and/or Gaucher disease. For example, research has indicated that glucocerebrosidase enzyme associated with various clinical phenotypes or types of Gaucher disease can be distinguished by differential interaction with various enzyme inhibitors. An inhibitor could be, e.g., a molecule or a binding moiety such as an antibody. In another example, distinct glucocerebrosidase enzymes have been shown to respond differently to various activating agents. For instance, activator lipids or acidic phospholipids, e.g., phosphatidylserine or bile salts, e.g., sodium taurocholate or sodium taurodeoxy-cholate. Members of another class of acidic lipids, namely gangliosides, and n-alkanols are also able to activate glucocerebrosidase enzyme to varying degrees. A reaction of glucocerebrosidase enzyme and substrate within the scope of the present invention may include any combination of inhibitors, activators, or other agents, including but certainly not limited to tissue or cell extracts.

Kits

The present invention includes kits for the determination of kinetic parameters relating glucocerebrosidase enzyme. In particular, certain kits of the present invention may include one or more of a glucocerebrosidase enzyme as described herein, a glucocerebrosidase substrate as described herein, or an apparatus for separation and/or detection as described herein, as well as reagents for the operation of an apparatus for separation and/or detection. For instance, a kit of the present invention may include a glucocerebrosidase substrate such as C18:1 glucosylceramide and an HPAEC-PAD apparatus. Kits can include an apparatus for in-line desalting, e.g., an apparatus including a reverse phase pre-column and an anion exchange analytical column, with or without instructions. Kits of the present invention may further include instructions for the use of the kit in determining kinetic parameters relating to a glucocerebrosidase enzyme. Components of the present invention or components required for the operation of the present invention may also be provided in a compact unit or portable device such as a table top, miniaturized, or hand-held device.

The invention will be more fully understood by reference to the following examples. They should not, however, be construed as limiting the scope of the invention. All literature citations are incorporated by reference.

EXAMPLES

The examples described herein demonstrate an exemplary process for determining kinetic parameters of glucocerebrosidase enzyme samples using a physiologically relevant substrate (FIG. 1). In particular, the below examples demonstrate the use of a velaglucerase alfa substrate, C18:1 glucosylceramide, to determine the kinetic parameters of velaglucerase. Cleavage of C18:1 glucosylceramide to produce glucose as one of the products is determined by HPAEC-PAD.

While the below examples are discussed in the context of testing experimental samples of enzyme, the below methods may be readily applied to the testing of various drug substances (DSs), drug products (DPs), or DS and DP stability samples.

Although exemplary embodiments have been described in detail, it should be understood that various changes, substitutions and alterations can be made herein without departing from the spirit and scope of the invention as defined in the appended claims.

Example 1

Preparation of Standard Curve Solutions

Dilutions of glucose molecules produced by or identical to the glucose product of the cleavage of the relevant substrate (C18:1 glucosylceramide) by glucocerebrosidase enzyme were produced for use in producing a reaction product standard curve. Glucose solutions were prepared by first mixing 40 µL of a 2 mM glucose stock with 760 µL Milli-Q water to yield 100 µM glucose, of which 250 µL were further diluted in 750 µL Milli-Q water to yield 25 µM glucose. A 20 µL aliquot of 25 µM glucose contains 500 picomoles glucose; this volume can be used for injections and the 25 µM glucose dilution can also be referred to as a 500 pmol/injection stock. The 25 µM glucose dilution can be stored at 2° C. to 8° C. for up to 3 weeks. The 25 µM glucose dilution was used to prepare the serial dilution series shown in Table 1. Glucose stocks stored in an autosampler apparatus, such as an autosampler apparatus that can be used in a method of chromatography, at 10° C. can be used for up to 7 days.

TABLE 1

Exemplary Standard Curve Preparation

| Dilution | Amount of glucose per 20 µL injection (picomoles) |
| --- | --- |
| A | 3.906 |
| B | 7.813 |
| C | 15.63 |
| D | 31.25 |
| E | 62.50 |
| F | 125.0 |
| G | 250.0 |
| H | 500.0 |

Example 2

Preparation of Substrate

Sonication was used to achieve a consistent substrate preparation. A sonicator was pre-set to 60% AMPL and 5 minutes. A 4 oz. amber bottle of substrate dilution buffer (4 mM taurocholic acid, 0.2% v/v oleic acid in citrate/phosphate buffer pH 5.0) was placed in the noise isolation chamber and the sonicator probe was immersed into the solution. The substrate dilution buffer was sonicated at 60% AMPL for 5 minutes. Following sonication, the noise isolation chamber was opened. A second cycle of sonication at 60% AMPL for 5 minutes was initiated while the amber bottle was gently swirled. After 5 minutes, the substrate dilution buffer was cloudy. Approximately 15-20 mg of C18:1 glucosylceramide was weighed in a clean 2 oz. amber bottle. Sonicated substrate dilution buffer was added to bring the concentration of C18:1 glucosylceramide to 0.64 mg/mL (approximately 880 µM). Next, the same sonication steps were repeated for the 2 oz. amber bottle of 880 µM C18:1 glucosylceramide, with the additional consideration that, prior to the step of gently swirling the bottle while sonicating, it was ensured that all substrate particles were in the biphasic mixture. Sonication and swirling were continued until there were no visible particles in the mixture.

After the sonication procedure, two stocks were prepared for use in the assay. A first reagent reservoir filled with sonicated substrate dilution buffer. A second reagent reservoir was filled with 6 mL sonicated substrate dilution buffer and 2 mL of the 880 µM C18:1 glucosylceramide (final substrate concentration of 220 µM C18:1 glucosylceramide).

A dilution series of substrate was prepared in a 96-well plate having columns 1-12, rows A-H, and a well volume of 0.5 mL. Each well of rows A-G was filled with 170 µL substrate dilution buffer. In addition, 200 µL substrate solution of different concentrations were transferred to the appropriate wells of rows A to G according to Table 2. Substrate dilution buffer and substrate solution were mixed by pipetting. Appropriate wells of row H were filled with 400 µL of 220 µM substrate solution as shown in Table 2.

TABLE 2

Exemplary Substrate dilutions

| Row of 96-well plate | Sample dilution buffer (µL) | Substrate solution (µL) | Substrate solution (µM) | Substrate in reaction (µM) |
| --- | --- | --- | --- | --- |
| A | 170 | 200 | 2.97 | 2.70 |
| B | 170 | 200 | 5.49 | 4.99 |
| C | 170 | 200 | 10.2 | 9.23 |
| D | 170 | 200 | 18.8 | 17.1 |
| E | 170 | 200 | 34.7 | 31.6 |
| F | 170 | 200 | 64.3 | 58.4 |
| G | 170 | 200 | 119 | 108 |
| H | 0 | 400 | 220 | 200 |

Example 3

Preparation of Samples

Frozen experimental and assay control samples were thawed in a 37° C. water bath for <5 min. In the present examples, the sample is a sample of enzyme. After thawing, each tube was placed on ice. Dilutions of the samples were then prepared at room temperature. To prepare the sample dilutions, sample dilution buffer (50 mM citrate buffer pH 6.0, 0.75 mg/ml BSA) was placed on ice in centrifuge tubes, each tube containing 990 µL sonicated sample dilution buffer. Tubes of sample dilution buffer were briefly vortexed (1-3 seconds) and pulse centrifuged to collect the liquid to the bottom of the tube. A 10 µL aliquot of each sample was transferred into a dedicated tube of sample dilution buffer to prepare a 1:100 dilution. Samples were diluted in triplicate. Samples were briefly vortexed to ensure proper mixing. Next, a 10 μL aliquot of each of 1:100 diluted sample was transferred to a dedicated second tube having been pre-loaded with 990 μL sample dilution buffer, resulting in a 1:10,000 dilution. Samples were briefly vortexed to ensure proper mixing. Next, the 1:10,000 dilution was used to prepare a 1 mL dilution having a final concentration of 0.02 ng/μL. In particular, the volume of the 1:10,000 dilution needed to dilute the enzyme to 0.02 ng/μL in 1 mL was determined and transferred from the second tube into the a third dedicated tube preloaded with an amount of sample dilution buffer calculated to result in a total volume of 1 mL at 0.02 ng/μL. Accordingly, when 10 μL of 0.02 ng/μL enzyme is mixed with 100 μL of substrate solution, the final concentration of enzyme is 0.0290 nM, assuming a monomer with a relative molecular mass of 62.8 kDa. Samples were briefly vortexed to ensure proper mixing. Final dilution tubes were placed on ice.

Example 4

Enzyme Reaction

Briefly, velaglucerase alfa was incubated with C18:1 glucosylceramide at eight concentrations of substrate (2.70-200 μM) and in 110 μL reactions for 20 min at 37° C. with appropriate standards and/or controls. The production of glucose reaction product was determined using HPAEC-PAD.

Figure 2:
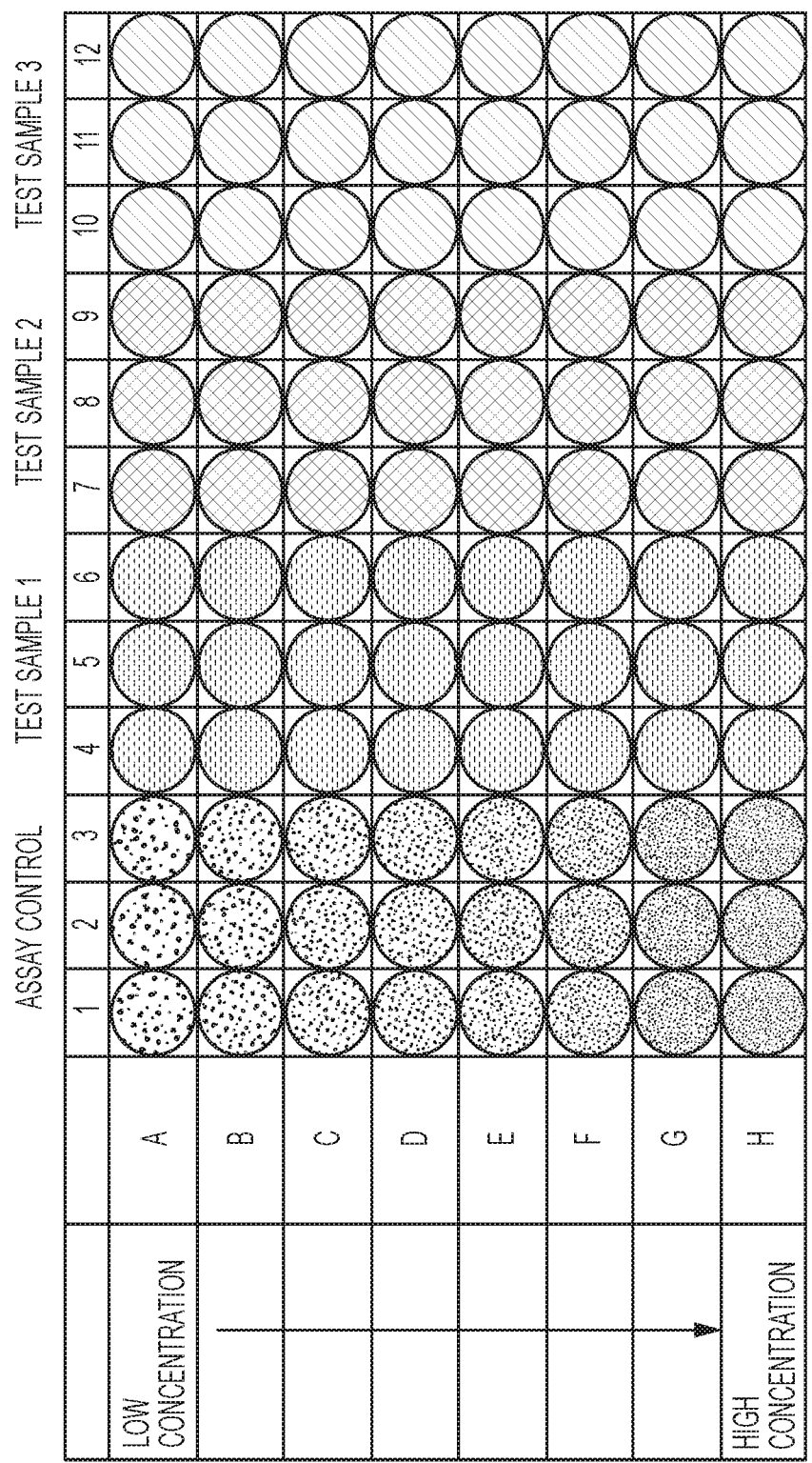
FIG. 2 is an exemplary diagram of a 96-well assay plate that includes three columns of assay control, three columns containing a first experimental sample, three columns containing a second experimental sample, and three columns containing a third experimental sample. Concentration increase from row A through row H.

A 96-well assay plate was placed on ice and 10 μL of each 0.02 ng/μL experimental and assay control enzyme sample were transferred to the appropriate wells of the assay plate according to FIG. 2. After being placed on the plate holder of the thermocycler, 100 μL of substrate solution were transferred from the dilution plate to the assay plate using a 12-channel pipette (working from Row A to Row H in as short time as possible). Accordingly, each reaction is prepared in triplicate and each sample is tested against eight concentrations of the substrate C18:1 glucosylceramide (2.70-200 μM). Wells were mixed by pipetting. The assay plate was sealed with PCR adhesive foil and thermocycled for 20 min at 37° C., followed by 10 min at 80° C. in order to heat-inactivate the enzyme, after which samples were held at 4° C. The assay plate was removed from the thermocycler and spun in a bench-top centrifuge for 2 min at 2,000×g. From each well of the PCR assay plate, 100 μL were transferred to the corresponding wells of a 96-well injection plate (Nunc U96 microwell plate) using a multi-channel pipette. The injection plate was covered with a Nalgene pre-slit well cap for Dionex HPAEC-PAD injection.

Example 5

Chromatography

Glucose product was analyzed by HPAEC-PAD. Prior to starting the sequence, the detector was turned on and the pump was set at 1.0 mL/min with 46% eluent A (10 mM sodium hydroxide solution), 46% eluent C (10 mM sodium hydroxide solution; both eluent A and C contain 10 mM sodium hydroxide), and 8% eluent B (500 mM sodium hydroxide) mobile phases. The signal was allowed to stabilize for >1 hour before the first injection.

Twenty microliters of each replicate of each sample were injected onto an NG-1 guard column preceding a PA-10 analytical column. An isocratic separation was achieved with 46% A, 46% C, and 8% B at a flow rate of 1.0 mL/min for 20 min. Samples were run on the instrument and each chromatograph was viewed in the Chromeleon Software Review screen. Data was analyzed to determine kinetic parameters according to Example 6. An example of HPAEC-PAD system settings are shown in Table 3.

TABLE 3

| Exemplary HPAEC-PAD setup | |
|---|---|
| System settings | |
| Sampler.AcquireExclusiveAccess | |
| Column_TC.AcquireExclusiveAccess | |
| Compartment_TC.AcquireExclusiveAccess | |
| Pressure.LowerLimit = | 50 [psi] |
| Pressure.UpperLimit = | 3800 [psi] |
| % A.Equate = | "% A 10 mM NaOH" |
| % B.Equate = | "% B 500 mM NaOH" |
| % C.Equate = | "% C 10 mM NaOH"" |
| % D.Equate = | "% D" |
| Pump_1_Pressure.Step = | Auto |
| Pump_1_Pressure.Average = | On |
| Flush Volume = | 400 |
| Wait FlushState | |
| NeedleHeight = | 3 [mm] |
| CutSegmentVolume = | 0 [μl] |
| SyringeSpeed = | 3 |
| TrayTemperature = | 10.00 |
| CycleTime = | 0 [min] |
| WaitForTemperature = | False |
| EDet1.Mode = | IntAmp |
| EDet1.CellControl = | On |
| Data_Collection_Rate = | 1.00 [Hz] |
| pH.UpperLimit = | 13.00 |
| pH.LowerLimit = | 10.00 |
| WaveformName = | "carbohydrates (standard quad)" |
| WaveformDescription = | "Carbohydrates (std. quad. potential)" |
| Electrode = | AgCl |
| Waveform Time = | 0.000 |
| Potential = | 0.100 |
| GainRegion = | Off |
| Ramp = | On |
| Integration = | Off |
| Waveform Time = | 0.200 |
| Potential = | 0.100 |
| GainRegion = | On |
| Ramp = | On |
| Integration = | On |
| Waveform Time = | 0.400 |
| Potential = | 0.100 |
| GainRegion = | Off |
| Ramp = | On |
| Integration = | Off |
| Waveform Time = | 0.410 |
| Potential = | −2.000 |
| GainRegion = | Off |
| Ramp = | On |
| Integration = | Off |
| Waveform Time = | 0.420 |
| Potential = | −2.000 |
| GainRegion = | Off |
| Ramp = | On |
| Integration = | Off |
| Waveform Time = | 0.430 |
| Potential = | 0.600 |
| GainRegion = | Off |
| Ramp = | On |
| Integration = | Off |
| Waveform Time = | 0.440 |
| Potential = | −0.100 |
| GainRegion = | Off |
| Ramp = | On |
| Integration = | Off |
| Waveform Time = | 0.500 |
| Potential = | −0.100 |
| GainRegion = | Off |
| Ramp = | On |
| Integration = | Off |
| LastStep = | On |
| Column_TC.Mode= | ON 30° C. |

TABLE 3-continued

Exemplary HPAEC-PAD setup

| | |
|---|---|
| Compartment_TC.Mode = | Off |
| Wait | SampleReady |
| 0.000 Flow = | 1.00 [ml/min] |
| % B = | 8.0 [%] |
| % C = | 46.0 [%] |
| % D = | 0.0 [%] |
| Curve = | 5 |
| Load | |
| Wait | CycleTimeState |
| Inject | |
| Wait | InjectState |
| EDet1.Autozero | |
| ED_1.AcqOn | |
| Pump_1_Pressure.AcqOn | |
| Sampler.ReleaseExclusiveAccess | |
| Compartment_TC.ReleaseExclusiveAccess | |
| Column_TC.ReleaseExclusiveAccess | |
| Flow = | 1.00 [ml/min] |
| % B = | 8.0 [%] |
| % C = | 46.0 [%] |
| % D = | 0.0 [%] |
| Curve = | 5 |
| 8.000 Flow = | 1.00 [ml/min] |
| % B = | 8.0 [%] |
| % C = | 46.0 [%] |
| % D = | 0.0 [%] |
| Curve = | 5 |
| 8.100 Flow = | 1.00 [ml/min] |
| % B = | 100.0 [%] |
| % C = | 0.0 [%] |
| % D = | 0.0 [%] |
| Curve = | 5 |
| 12.000 Flow = | 1.00 [ml/min] |
| % B = | 100.0 [%] |
| % C = | 0.0 [%] |
| % D = | 0.0 [%] |
| Curve = | 5 |
| 12.100 Flow = | 1.00 [ml/min] |
| % B = | 8.0 [%] |
| % C = | 46.0 [%] |
| % D = | 0.0 [%] |
| Curve = | 5 |
| 20.000 Pump_1_Pressure.AcqOff | |
| Flow = | 1.00 [ml/min] |
| ED_1.AcqOff | |
| % B = | 4.0 [%] |
| % C = | 0.0 [%] |
| % D = | 0.0 [%] |
| Curve = | 5 |
| End | |

Example 6

Data Analysis

The glucose product present in each injection was quantified by comparing to a standard curve (3.91-500 pmol/injection), and the rate of product formation was plotted against the substrate concentration. To analyze the product standard curve, a linear regression curve of the peak area vs. the glucose product standard concentration (µM) was generated. The slope, intercept and $R^2$ value were determined and recorded. To analyze the negative control, the peak area of the negative control (substrate in substrate dilution buffer) was entered. In order to calculate the velocities from the product peak areas, the peak area was converted to concentration (using the standard curve parameters) for each injection of sample at each substrate concentration and dividing by 20 minutes.

In order to determine the values $k_{cat}$ and $K_m$, each replicate velocity and the corresponding substrate concentration were entered in a software that can perform non-linear regression. The data were fitted to the Michaelis-Menten model to obtain $V_{max}$ (µM/min) and $K_m$ (µM), and $k_{cat}$ (s$^{-1}$) was calculated by dividing $V_{max}$ with the enzyme concentration [E] (µM). A non-linear regression fit was performed using the Michaelis-Menten equation:

$$v_0 = \frac{V_{max}[S]}{K_m + [S]}$$

$V_{max}$ was divided with the total enzyme concentration in the reaction and divided by 60 seconds/minute to obtain $k_{cat}$ (s$^{-1}$). The enzyme concentration in the reaction, used for calculating $k_{cat}$ from $V_{max}$ for velaglucerase was 2.90×10$^{-5}$ µM. This value was calculated based on a molecular mass of 62.8 kDa.

Example 7

Determination of Kinetic Parameters using an NBD-C6 Substrate

Figure 3A:
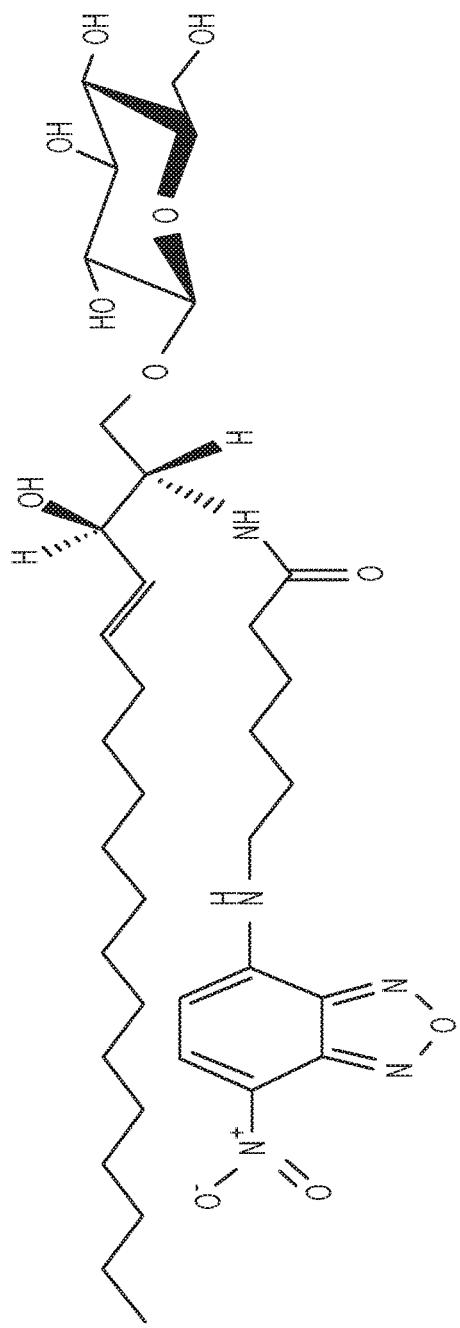
FIG. 3A is an exemplary schematic of a glucocerebrosidase substrate.
Figure 3B:
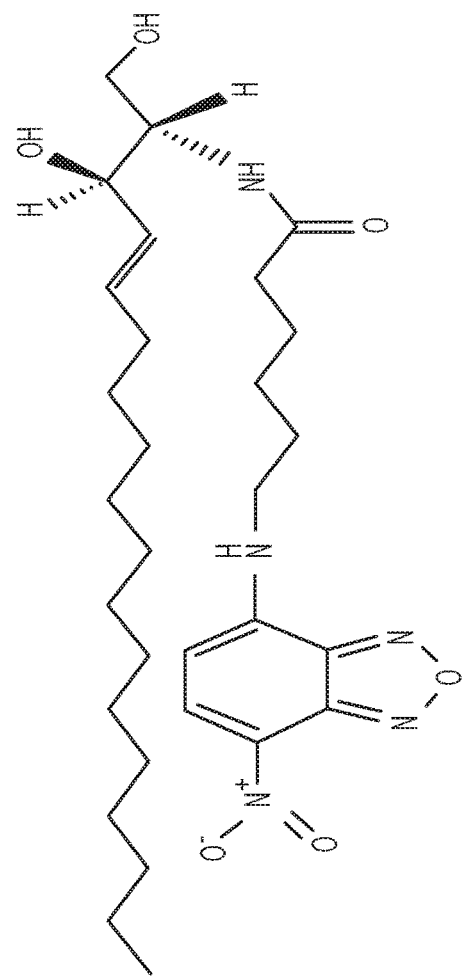
FIG. 3B is a schematic of a product that can be generated by the cleavage of the substrate of FIG. 3A by glucocerebrosidase enzyme.
Figure 4:
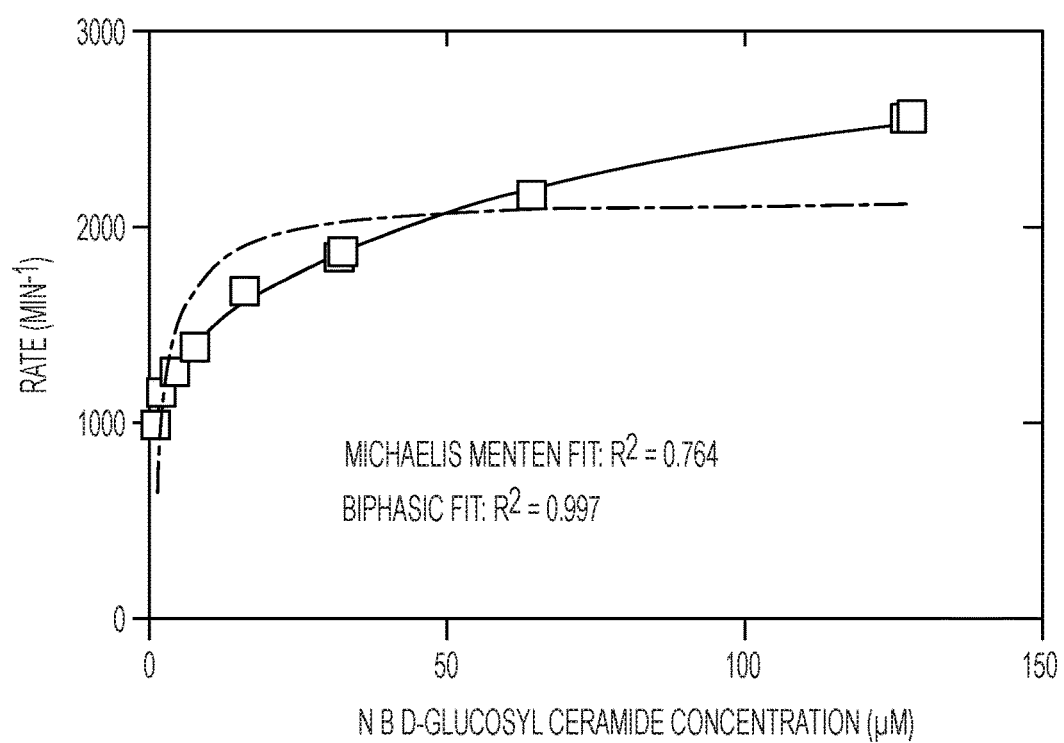
FIG. 4 is an exemplary graph showing a curve fit to data generated from multiple concentrations of NBD-glucosylceramide. As indicated in the figure, the data can be fit by Michaelis-Menten ($R^2=0.764$) or a biphasic fit ($R^2=0.997$).
Figure 5:
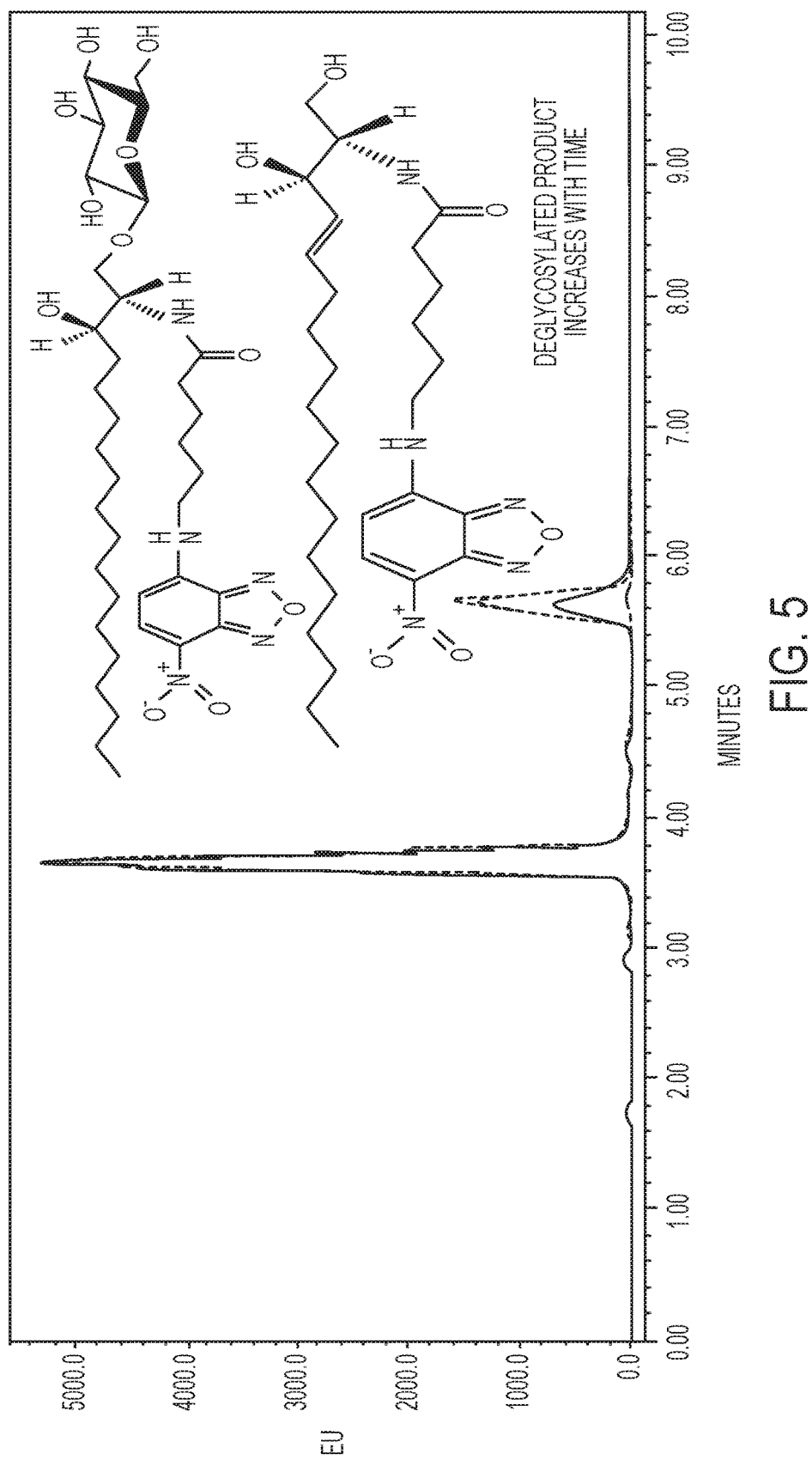
FIG. 5 is an exemplary result of a chromatographic analysis in which two major peaks locations are observed. A right-hand peak represents the a glucocerebrosidase substrate NBD-glucosylceramide and the left-hand peak represents a product produced by the cleavage of that substrate by a glucocerebrosidase enzyme.

In another Example, the invention includes an assay of glucocerebrosidase enzyme activity in which the substrate is NBD-Glycosylceramide. In such substrates, the spacer between the NBD fluorophore and the amide bond can vary. As shown in FIG. 3A, in some instances, NBD-Glycosylceramide has a C6 spacer. When incubated with velaglucerase, cleavage of the substrate produces the product shown in FIG. 3B. Here, NBD-C6 substrate was dissolved in assay buffer with sonication and detergents. NBD-C6 was then incubated with velaglucerase for 20 minutes. The reaction was stopped by the addition of a two-fold volume of acetonitrile. Samples were analyzed by UPLC (10 minutes/injection). Appropriate controls and standard curve dilutions were included in the assay. The resulting data were plotted using the Michaelis-Menten model (FIG. 4). Results demonstrate that deglycosylated product increased with time (FIG. 5).

Example 8

Figure 6:
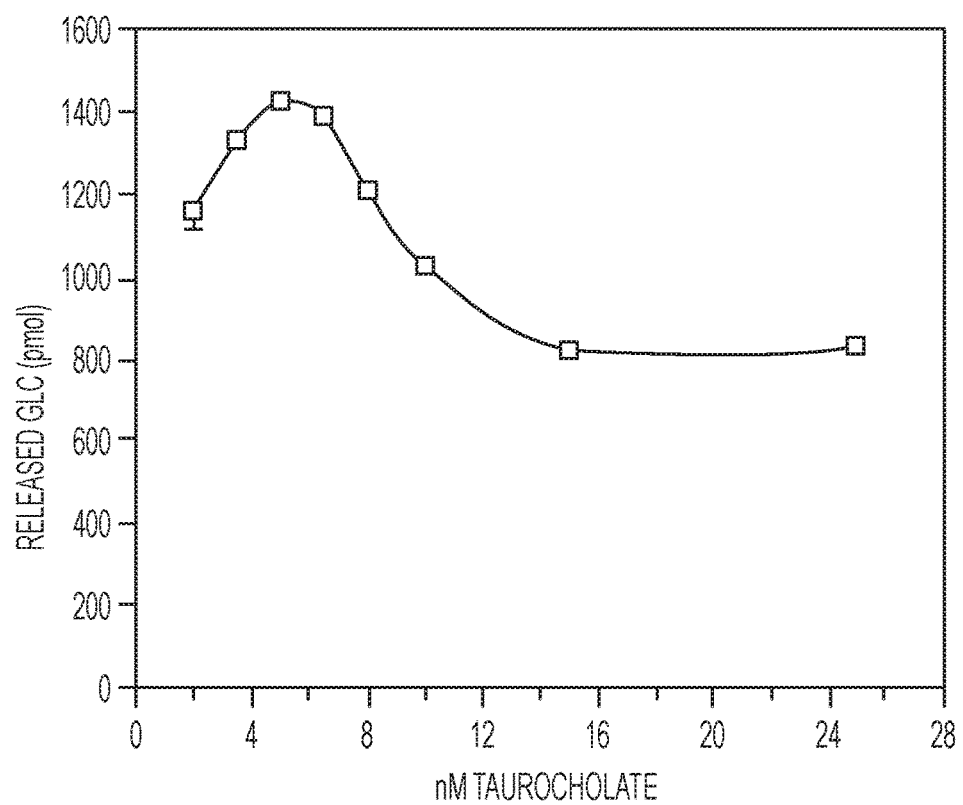
FIG. 6 is an exemplary graph of the response of velaglucerase activity to the concentration of sodium taurocholate under particular conditions.
Figure 7:
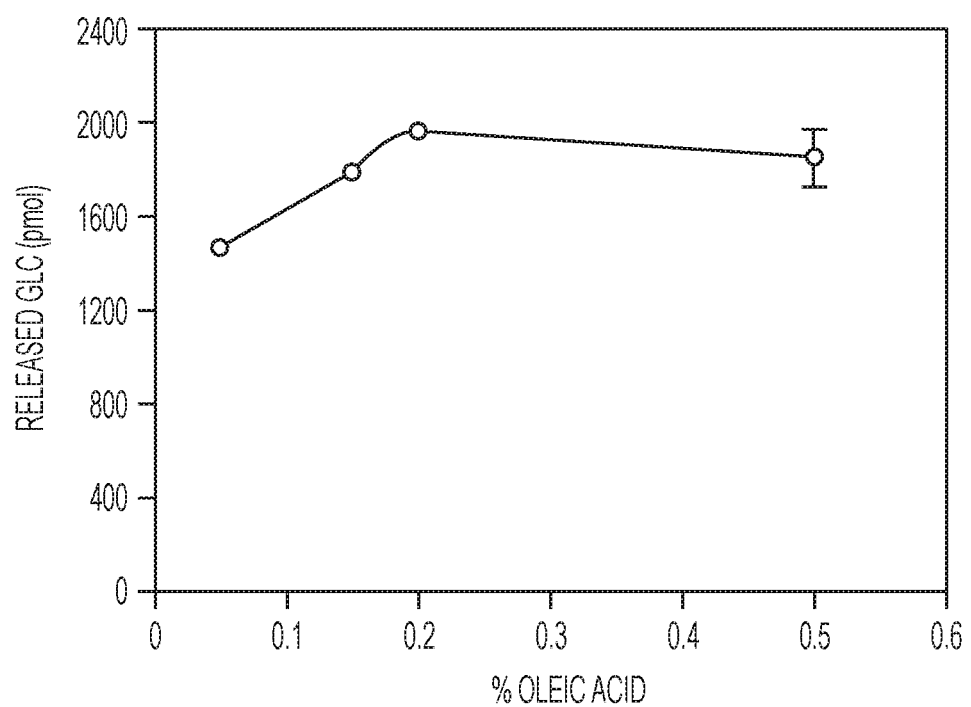
FIG. 7 is an exemplary graph of the response of velaglucerase activity to the concentration of oleic acid under particular conditions.

Analysis of Relationship Sodium Taurocholate or Oleic Acid to Velaglucerase Activity Assays of velaglucerase activity were carried out in the presence of varying levels of sodium taurocholate or oleic acid. Sodium taurocholate is an anionic detergent that has been, in some cases, used to facilitate lipid-based substrate solubility in aqueous environments. The effect of sodium taurocholate was examined over a concentration range of 2 mM to 25 mM (FIG. 6). Results suggested that, under the experimental conditions applied and over the range of concentrations tested, maximum activity occurred between 5 mM and 6.5 mM sodium taurochlorate, and that the activity gradually declined at concentrations of sodium taurocholate above 8 mM. This experiment suggested that, under the tested conditions, an optimal concentration of sodium taurocholate was 6.5 mM. Experiments exploring different concentrations of oleic acid suggested use of amounts of oleic acid ranging from 0.05%, or even less than 0.05%, to at least 0.5% may be used in velaglucerase reactions under the applied experimental conditions.

Example 9

Monitoring Degradation of Velaglucerase

Samples subjected to forced degradation were tested to illustrate how velaglucerase kinetic parameters can be determined and applied using the method described in the previous examples. A condition was selected that was known to induce degradation of velaglucerase: oxidation by light exposure (photo stress). A clear decrease in $k_{cat}$ was observed for the stressed sample (Table 4). Under the specific conditions of the present example, the minor increase in $K_m$ was not considered significant (Table 4).

TABLE 4

Forced degradation of velaglucerase is detected using an enzyme kinetics assay; baseline is an unstressed control

| Sample | $k_{cat}$ (s$^{-1}$) | $K_m$ (μM) |
|---|---|---|
| Baseline | 90.7 | 4.9 |
| Photo Stress | 76.8 | 6.7 |

Other Embodiments

While we have described a number of embodiments of this invention, it is apparent that our basic disclosure and examples may be altered to provide other embodiments that utilize the compounds and methods of this invention. Therefore, it will be appreciated that the scope of this invention is to be defined by the appended claims rather than by the specific embodiments that have been represented by way of example. All references cited herein are hereby incorporated by reference.

What is claimed is:

1. A method of determining potency of glucocerebrosidase, comprising the steps of:
   contacting a sample comprising a glucocerebrosidase with a C18:1 β-D-Glucosylceramide substrate under conditions that permit the glucocerebrosidase to catalyze hydrolysis of the C18:1 β-D-Glucosylceramide substrate to release glucose; and
   measuring the amount of glucose released to determine one or more kinetic parameters of the glucocerebrosidase,
   wherein the one or more kinetic parameters are selected from the group consisting of $V_{max}$, $k_{cat}$, $K_m$, and specific activity,
   wherein the one or more kinetic parameters are indicative of the potency of the glucocerebrosidase.

2. The method of claim 1, wherein the glucocerebrosidase is a recombinant glucocerebrosidase.

3. The method of claim 2, wherein the recombinant glucocerebrosidase is velaglucerase alfa.

4. The method of claim 1, wherein the step of measuring the amount of glucose released comprises performing chromatography.

5. The method of claim 4, wherein the chromatography comprises high-performance liquid chromatography (HPLC) or ultra performance liquid chromatography (UPLC).

6. The method of claim 4, wherein said chromatography includes anion exchange chromatography.

7. The method of claim 4, wherein the step of measuring the amount of glucose released comprises performing high-performance anion exchange chromatography coupled to pulsed amperometric detection (HPAEC-PAD).

8. The method of claim 1, wherein the step of measuring the amount of glucose released comprises determining the amount of glucose as compared to a control.

9. The method of claim 8, wherein the control is a predetermined amount of glucose.

10. The method of claim 8, wherein the control is a standard curve.

11. The method of claim 1, wherein the step of measuring the amount of glucose released comprises determining the rate of glucose formation.

12. The method of claim 1, wherein the one or more kinetic parameters are determined by fitting the amount of glucose released to the Michaelis-Menten model or other kinetic model suitable to determine kinetic parameters.

13. The method of claim 1, wherein the substrate is sonicated prior to said contacting.

14. The method of claim 13, wherein the substrate is sonicated for about 1 to 10 minutes.

15. The method of claim 1, wherein the sample is a drug substance, a drug product, or a stability sample of drug substance and drug product.

16. The method of claim 1, wherein the conditions that permit the glucocerebrosidase to catalyze the substrate to release glucose comprise incubation at about 37° C. for about 20 minutes.

17. The method of claim 1, wherein the conditions that permit the glucocerebrosidase to catalyze hydrolysis of the substrate to release glucose comprise taurocholic acid and/or oleic acid.

18. The method of claim 17, wherein the taurocholic acid is included.

19. The method of claim 18, wherein the taurocholic acid is included at a concentration of about 0.5 to 100 mM.

20. The method of claim 18, wherein the taurocholic acid is included at a concentration of about 2 to 10 mM.

21. The method of claim 18, wherein the taurocholic acid is included at a concentration of 2 to 7 mM.

22. The method of claim 17, wherein the oleic acid is included.

23. The method of claim 22, wherein the oleic acid is included at a concentration of about 0.001% to 5% v/v.

24. The method of claim 22, wherein the oleic acid is included at a concentration of about 0.1% to 0.5% v/v.

25. The method of claim 22, wherein the oleic acid is included at a concentration of about 0.1% to 0.3% v/v.

26. The method of claim 1, wherein the method further comprises a step of inactivation of the glucocerebrosidase.

27. The method of claim 1, wherein the method comprises a step of removing lipids from an enzyme sample prior to measuring the amount of glucose released.

28. The method of claim 27, wherein the step of removing lipids comprises in-line desalting.

* * * * *

SEQUENCE LISTING

```
<160> NUMBER OF SEQ ID NOS: 3

<210> SEQ ID NO 1
<211> LENGTH: 400
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255
```

```
Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
            290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
            325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
            355                 360                 365

Thr Asn Leu Leu Tyr His Val Gly Trp Thr Asp Trp Asn Leu Ala
            370                 375                 380

Leu Asn Pro Glu Gly Gly Pro Asn Trp Val Arg Asn Phe Val Asp Ser
385                 390                 395                 400

<210> SEQ ID NO 2
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
            85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
            165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
```

```
                210                 215                 220
Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
                260                 265                 270

His His Asn Val Arg Leu Leu Met Leu Asp Asp Gln Arg Leu Leu Leu
                275                 280                 285

Pro His Trp Ala Lys Val Val Leu Thr Asp Pro Glu Ala Ala Lys Tyr
                290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
                340                 345                 350

Arg Leu Gly Ser Trp Asp Arg Gly Met Gln Tyr Ser His Ser Ile Ile
                355                 360                 365

Thr Asn Leu Leu Tyr His Val Val Gly Trp Thr Asp Trp Asn Leu Ala
                370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
                420                 425                 430

Arg Val Gly Leu Val Ala Ser Gln Lys Asn Asp Leu Asp Ala Val Ala
                435                 440                 445

Leu Met His Pro Asp Gly Ser Ala Val Val Val Leu Asn Arg Ser
                450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 3
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
                35                  40                  45

Met Glu Leu Ser Met Gly Pro Ile Gln Ala Asn His Thr Gly Thr Gly
                50                  55                  60
```

```
Leu Leu Leu Thr Leu Gln Pro Glu Gln Lys Phe Gln Lys Val Lys Gly
 65                  70                  75                  80

Phe Gly Gly Ala Met Thr Asp Ala Ala Ala Leu Asn Ile Leu Ala Leu
                 85                  90                  95

Ser Pro Pro Ala Gln Asn Leu Leu Lys Ser Tyr Phe Ser Glu Glu
            100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
        130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
        210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
        290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
        370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
        450                 455                 460

Ser Lys Asp Val Pro Leu Thr Ile Lys Asp Pro Ala Val Gly Phe Leu
465                 470                 475                 480
```

```
Glu Thr Ile Ser Pro Gly Tyr Ser Ile His Thr Tyr Leu Trp Arg Arg
            485                 490                 495
Gln
```